United States Patent
Sheldon et al.

(10) Patent No.: US 9,861,739 B2
(45) Date of Patent: Jan. 9, 2018

(54) SYSTEMS AND METHODS FOR ACCESSING THE LUMEN OF A VESSEL

(71) Applicant: Houston Medical Robotics, Inc., Houston, TX (US)

(72) Inventors: Jeffery J. Sheldon, League City, TX (US); Kenneth R. Smith, League City, TX (US); Bruce W. Dannecker, League City, TX (US); Joseph M. Lacey, Hartselle, AL (US); Katherine E. Goodwin, Houston, TX (US)

(73) Assignee: HOUSTON MEDICAL ROBOTICS, INC., Houston, TX (US)

( * ) Notice: Subject to any disclaimer, the term of this patent is extended or adjusted under 35 U.S.C. 154(b) by 1277 days.

(21) Appl. No.: 13/773,878

(22) Filed: Feb. 22, 2013

(65) Prior Publication Data
US 2013/0261553 A1 Oct. 3, 2013

Related U.S. Application Data

(63) Continuation-in-part of application No. 13/080,318, filed on Apr. 5, 2011, and a continuation-in-part of
(Continued)

(51) Int. Cl.
*A61B 5/05* (2006.01)
*A61M 5/14* (2006.01)
(Continued)

(52) U.S. Cl.
CPC .............. *A61M 5/14* (2013.01); *A61B 8/0841* (2013.01); *A61B 8/4209* (2013.01); *A61B 17/3403* (2013.01); *A61B 90/11* (2016.02); *A61M 25/0113* (2013.01); *A61M 25/09041* (2013.01); *A61B 8/0891* (2013.01); *A61B 8/461* (2013.01); *A61B 2017/3407* (2013.01);
(Continued)

(58) Field of Classification Search
None
See application file for complete search history.

(56) References Cited

U.S. PATENT DOCUMENTS

| | | |
|---|---|---|
| 4,733,661 A | 3/1988 | Palestrant |
| 4,899,756 A | 2/1990 | Sonek |

(Continued)

FOREIGN PATENT DOCUMENTS

| | | |
|---|---|---|
| WO | 2006120619 | 11/2006 |
| WO | 2010006335 | 1/2010 |

OTHER PUBLICATIONS

Information Disclosure Statement submitted for U.S. Appl. No. 12/502,038, dated Dec. 30, 2009.
(Continued)

*Primary Examiner* — Joel F Brutus
(74) *Attorney, Agent, or Firm* — Winstead PC

(57) ABSTRACT

An apparatus for accessing the lumen of a vessel. The apparatus includes a handheld device and a cartridge. The handheld device includes an imaging device attachment utilized to secure an image capturing instrument, an arm coupled to the imaging device attachment. The cartridge includes a sheath, needle or guidewire coupled to the cartridge. The sheath or needle extends to the insertion depth when fully advanced, thereby allowing the sheath, needle, or guidewire to access the lumen of a vessel.

22 Claims, 19 Drawing Sheets

Related U.S. Application Data application No. 13/080,348, filed on Apr. 5, 2011, and a continuation-in-part of application No. 13/080,370, filed on Apr. 5, 2011.

(51) Int. Cl.

| | | |
|---|---|---|
| *A61B 8/08* | (2006.01) | |
| *A61B 8/00* | (2006.01) | |
| *A61B 17/34* | (2006.01) | |
| *A61M 25/09* | (2006.01) | |
| *A61B 90/11* | (2016.01) | |
| *A61M 25/01* | (2006.01) | |
| *A61M 25/06* | (2006.01) | |
| *A61B 90/00* | (2016.01) | |

(52) U.S. Cl.
CPC . *A61B 2017/3413* (2013.01); *A61B 2090/062* (2016.02); *A61B 2090/378* (2016.02); *A61M 25/0111* (2013.01); *A61M 25/065* (2013.01)

(56) References Cited

U.S. PATENT DOCUMENTS

| | | | |
|---|---|---|---|
| 5,389,083 A * | 2/1995 | McCarthy | A61M 5/3213 604/192 |
| 5,572,999 A | 11/1996 | Funda et al. | |
| 5,647,373 A | 7/1997 | Paltieli | |
| 6,193,657 B1 | 2/2001 | Drapkin | |
| 6,695,786 B2 | 2/2004 | Wang et al. | |
| 6,835,193 B2 | 12/2004 | Epstein et al. | |
| 7,166,075 B2 | 1/2007 | Varghese et al. | |
| 7,691,103 B2 | 4/2010 | Fernandez et al. | |
| 7,766,839 B2 | 8/2010 | Rogers et al. | |
| 7,890,155 B2 | 2/2011 | Burns et al. | |
| 7,976,469 B2 | 7/2011 | Bonde et al. | |
| 8,066,644 B2 | 11/2011 | Sarkar et al. | |
| 8,235,908 B2 | 8/2012 | Roschak et al. | |
| 2002/0177789 A1 | 11/2002 | Ferry et al. | |
| 2003/0233046 A1 | 12/2003 | Ferguson et al. | |
| 2004/0267121 A1 | 12/2004 | Sarvazyan et al. | |
| 2006/0111692 A1 | 5/2006 | Hlavka et al. | |
| 2006/0111733 A1 | 5/2006 | Shriver | |
| 2006/0116904 A1 | 6/2006 | Brem | |
| 2007/0135803 A1 | 6/2007 | Belson | |
| 2007/0137372 A1 | 6/2007 | Devengenzo et al. | |
| 2007/0185485 A1 | 8/2007 | Hauck et al. | |
| 2007/0233045 A1 | 10/2007 | Weitzner et al. | |
| 2008/0140087 A1 | 6/2008 | Barbagli | |
| 2008/0146918 A1 | 6/2008 | Magnin et al. | |
| 2008/0275396 A1 | 11/2008 | Neerken et al. | |
| 2009/0105597 A1 | 4/2009 | Abraham | |
| 2009/0125009 A1 | 5/2009 | Zikorus et al. | |
| 2009/0247993 A1 | 10/2009 | Kirschenman et al. | |
| 2010/0010505 A1 | 1/2010 | Herlihy et al. | |
| 2010/0036245 A1 | 2/2010 | Yu et al. | |
| 2010/0256558 A1 | 10/2010 | Olson et al. | |
| 2012/0197132 A1 | 8/2012 | O'Connor | |
| 2012/0259219 A1 | 10/2012 | Sheldon et al. | |
| 2012/0259220 A1 | 10/2012 | Sheldon et al. | |
| 2012/0259221 A1 | 10/2012 | Sheldon et al. | |

OTHER PUBLICATIONS

International Search Report and Written Opinion for PCT/US12/32310 dated Aug. 10, 2012.

International Search Report and Written Opinion for PCT/US12/32346 dated Aug. 3, 2012.

International Search Report and Written Opinion for PCT/US12/32355 dated Aug. 3, 2012.

\* cited by examiner

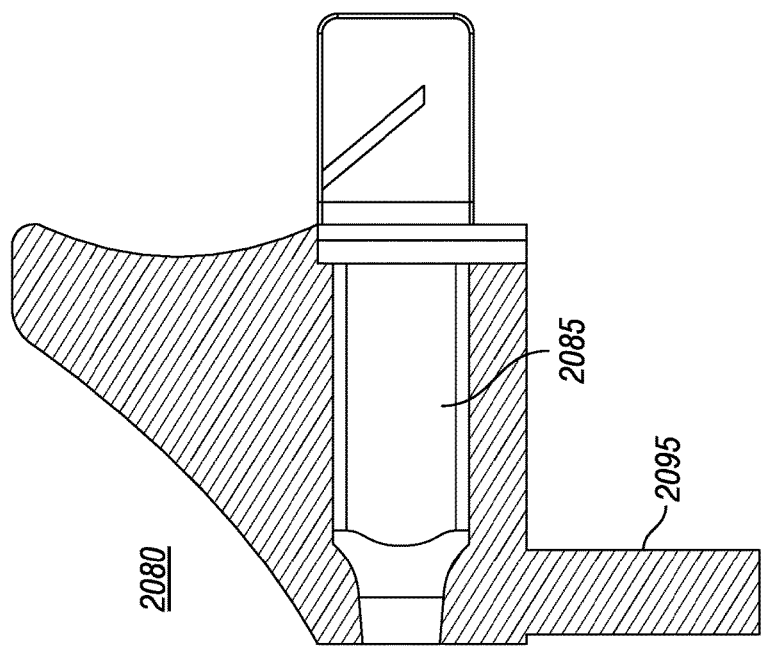
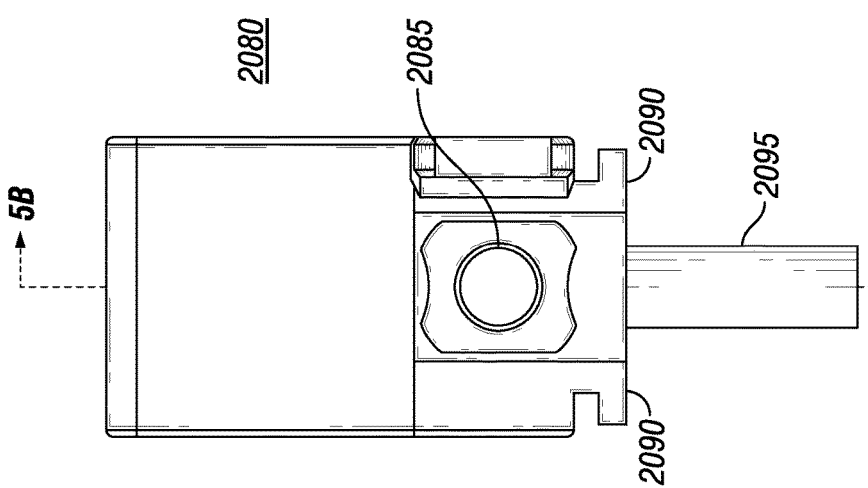
FIG. 5B
FIG. 5A

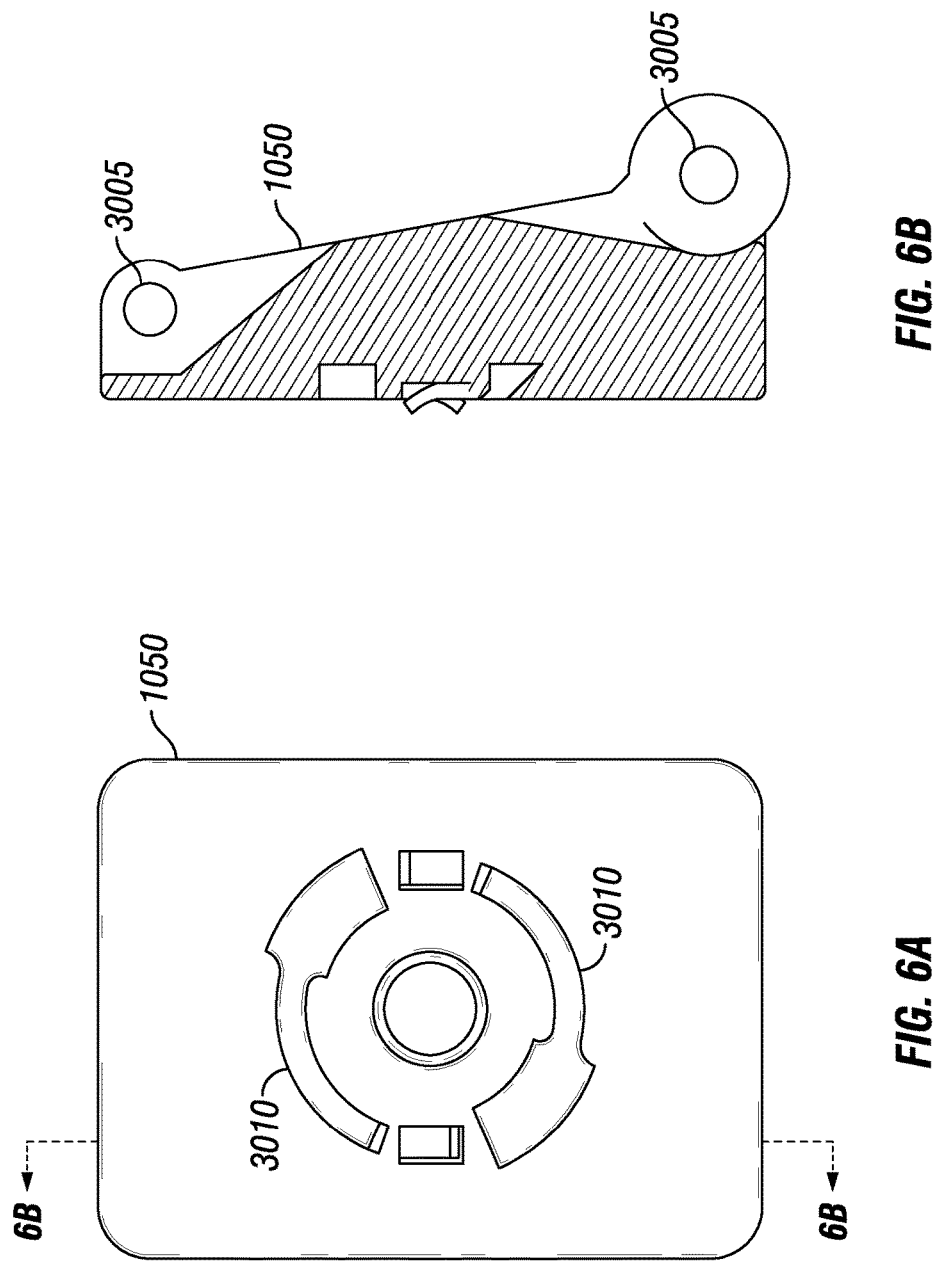

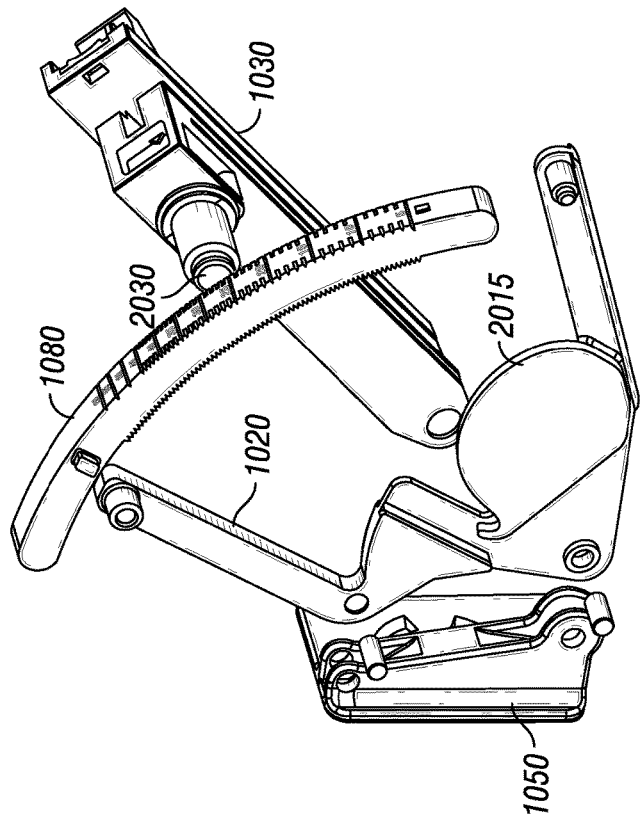
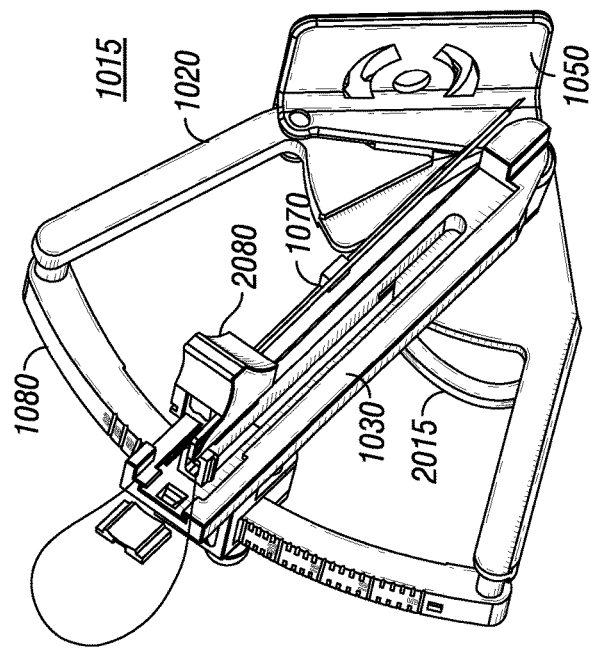
FIG. 7A
FIG. 7B

SYSTEMS AND METHODS FOR ACCESSING THE LUMEN OF A VESSEL

RELATED APPLICATIONS

This application is a Continuation-in-Part of U.S. patent application Ser. No. 13/080,318 filed on Apr. 5, 2011, which is incorporated herein by reference. This application is also a Continuation-in-Part of U.S. patent application Ser. No. 13/080,348 filed on Apr. 5, 2011 which is incorporated herein by reference. This application is also a Continuation-in-Part of U.S. patent application Ser. No. 13/080,370 filed on Apr. 5, 2011, which is incorporated herein by reference.

STATEMENT REGARDING FEDERALLY SPONSORED RESEARCH

Not Applicable

FIELD OF THE INVENTION

This invention relates to imaging assisted access of the lumen of vessels. More particularly, systems and methods discussed herein are related to the placement of a sheath, needle, and/or guidewire in a vessel.

BACKGROUND

Medical treatment may require the placement of catheters or the like into a person's body. For example, central venous catheters (also referred to herein as "CVC") are placed in a large vein for a variety of medical purposes. A series of manually performed steps to accomplish CVC placement have remained largely unchanged to date. First, a hollow introducer needle is manually inserted through the skin and placed in the vein. Second, a guide wire is manually inserted through the hollow of the needle into the lumen of the vein. The guide wire is inserted until a portion of the guide wire extends past the end of the needle. In this position, the distal end of the wire is in the central vein and the proximal end is outside the patient's body. The introducer needle, which at this point has the guide wire running through its length, is then removed from the patient by pulling the needle out and over the wire. During removal of the needle, the distal end of the guide wire is undisturbed inside the lumen of the vein. Third, the hollow CVC is placed over the proximal end of the guide wire, and the CVC advanced along the wire, through the skin, the subcutaneous tissues, and into the vein. At its final position, the catheter will have one end in the vein and the other end outside of the body. The guide wire can now be retrieved by pulling the guide wire through the catheter and out of the body, without disturbing the position of the catheter. The catheter can now be used to access to the central venous circulation. This process relies on the medical practitioner to locate the vein and may require several attempts before the CVC is properly placed. Similarly, other medical procedures may require placement of a sheath, needle, and/or guidewire into the lumen of a vessel. Medical practitioners may encounter similar problems when attempting to place a sheath, needle, and/or guidewire into the lumen of a vessel.

More recently, ultrasound has been used to assist in the placement of a CVC in a vein. Ultrasound can be used to locate the venous lumen and provide a visual target. The CVC may be placed manually or a robotic device may be used to place the CVC. Even with ultrasound guidance, a medical practitioner may fail to properly place the CVC. Further, current robotic devices are significantly large, cumbersome, and costly and their use in the placement of CVC is impractical.

SUMMARY

In an illustrative implementation, an apparatus for accessing a lumen of a vessel comprises an arm providing a cartridge and a body providing an image device attachment, wherein said arm is pivotally attached to said body, and the image device attachment is positioned adjacent to a pivot point of said arm. The apparatus may also include a slider coupled to the cartridge, wherein said slider secures a needle. The needle extends to the insertion depth when fully advanced, thereby allowing the needle or guidewire to access the lumen of a vessel. In some embodiments, said arm may be motorized to allow the arm to be adjusted to a desired position. Additionally, the needle or guidewire may be motorized to control advancement or retraction.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 5A-5B are illustrative implementations of a slider;

FIGS. 6A-6B are illustrative implementations of a transducer adapter mount;

FIGS. 7A-7B are illustrative implementations of a handheld device in an assembled view and a disassembled view;

DETAILED DESCRIPTION

Figure 1:
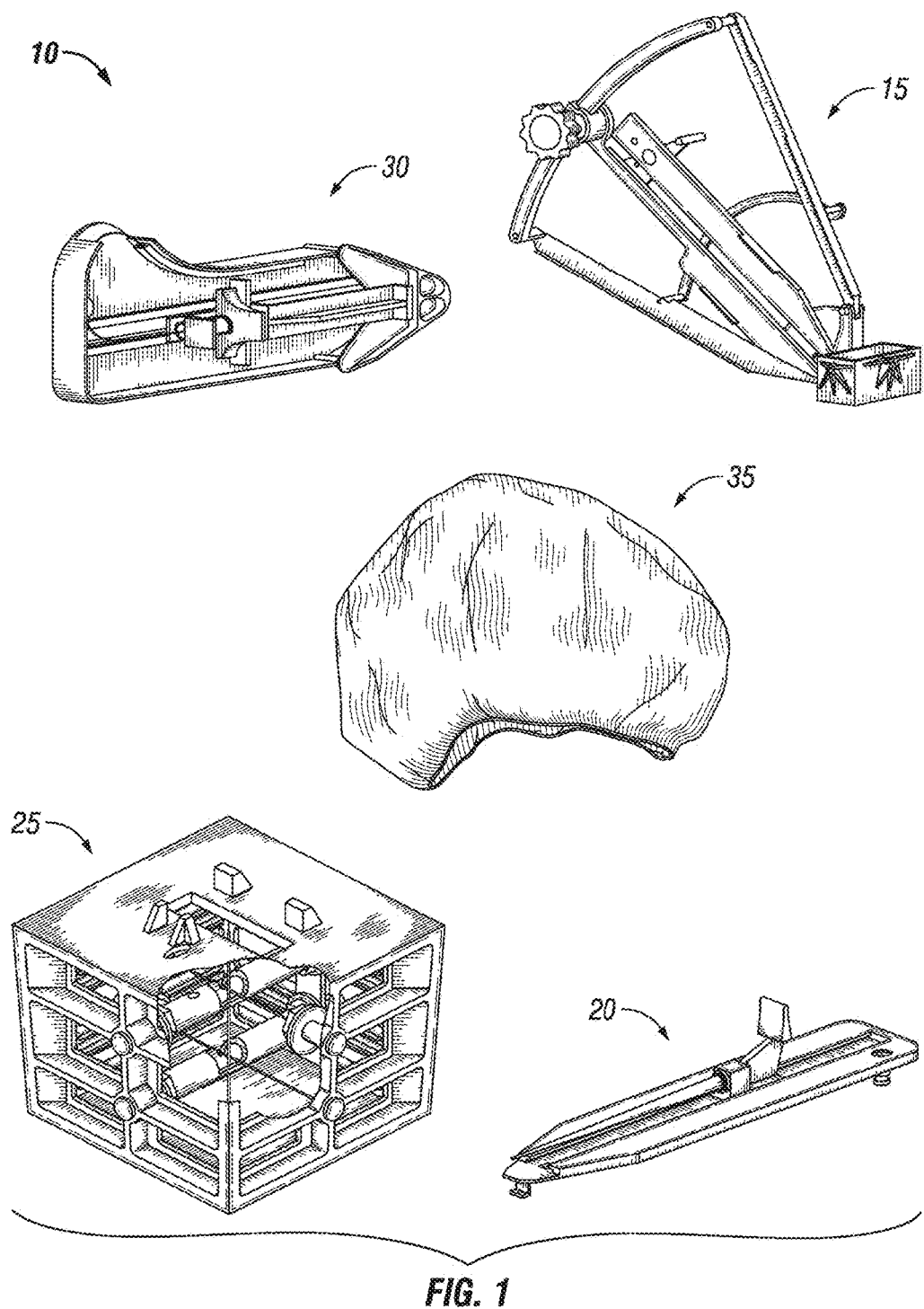
FIG. 1 is an illustrative implementation of an insertion system.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The systems and methods discussed herein are designed to integrate with a commercially available imaging system (e.g. ultrasound system) to provide a medical practitioner with the capability to accurately and reliably accessing the lumen of a vessel located at a depth of 5 mm to 60 mm below the skin surface. For example, the systems and methods discussed herein may be utilized to place a central venous catheter (CVC). While the implementations discussed herein may discuss usage of the systems and methods for starting a CVC, it will be recognized by one of ordinary skill in the art that the scope of the invention is in no way limited to starting a CVC. For example, in other implementations, the system may be utilized to place needle in a vessel; to place a guidewire via a needle placed in a vessel; or to place a sheath via a guidewire that is placed in a vessel via a needle. The systems and methods discussed herein may be utilized in a variety of medical procedures, including, but not limited to: CVC placement, peripherally inserted central catheters, phlebotomy, dialysis access, cardiac catheterization, amniocentesis, cholecystotomy, thoracentesis, paracentesis, and tracheostomy.

FIG. 1 is an illustrative implementation of an insertion system 10. In some embodiments, insertion system 10 may include a handheld device 15, alignment cartridge 20, alignment cube 25, sterile disposable cartridge 30, and cover 35. Handheld device 15 provides for proper alignment of the sheath, needle, and/or guidewire to be inserted into a vessel. Alignment cartridge 20 can be coupled to handheld device 15 and is utilized to perform a check on the alignment of handheld device 15. Alignment cube 25 is utilized to properly align an imaging system (not shown) coupled to handheld device 15. Disposable cartridge 30 can be coupled to handheld device 15 and may include a needle, guidewire, dilator, sheath, and/or other components utilized to place a CVC or the like. In some embodiments, sterile cover 35 may be place on handheld device 15 or a portion of handheld device 15 to prevent contamination or the like. In some embodiments, sterile cover 35 may also be place on an imaging device. Sterile cover 35 may be placed on or around handheld device 15 and disposed of after usage.

While the embodiment shown in FIG. 1 provides a disposable cartridge 30 that is removable from handheld device 15, in another embodiment of an insertion system a cartridge may be incorporated with the arm of the handheld device. The combined cartridge and arm may be desirable to reduce complexity of the manufacturing process. In some embodiments, the combined cartridge does not allow removal of the cartridge from the arm. The combined cartridge and arm provides the same features as disposable cartridges discussed herein. Throughout the disclosure the combined cartridge and arm may be interchangeably referred to as a combined cartridge, combined arm, arm, or cartridge. Further, it will be recognized that references to a cartridge, without specifying whether the cartridge is disposable or combined, indicate that said cartridge may be either a disposable cartridge or combined cartridge.

Figure 2A:
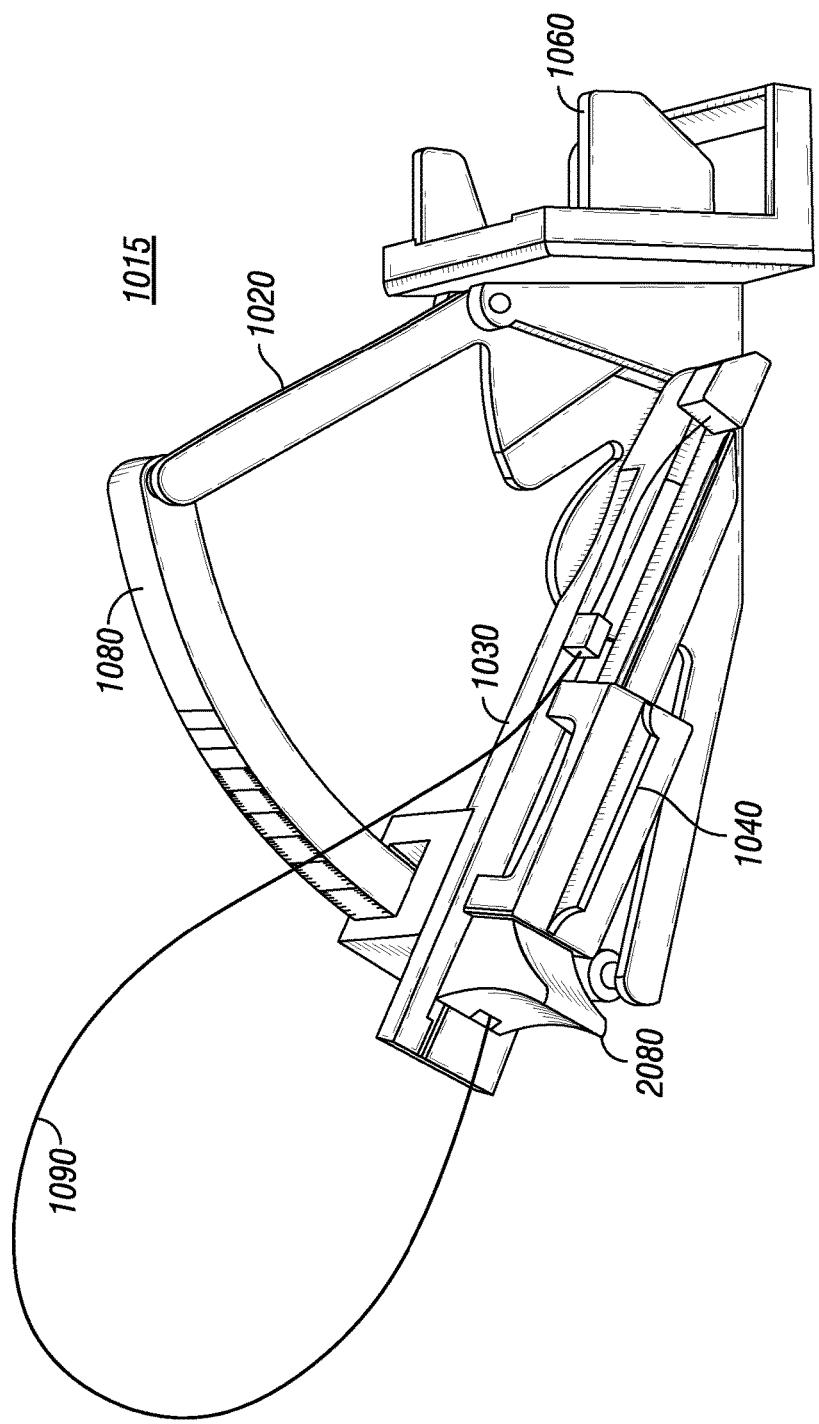
FIGS. 2A-2E are illustrative implementations of handheld devices.

FIG. 2A is an illustrative implementation of a handheld device 1015 with a combined cartridge and arm 1030. Handheld device 1015 may provide a frame assembly 1020, combined cartridge 1030, transducer adapter 1060, and depth scale 1080. Frame assembly 1020 provides a main body of the handheld device 1015. The frame assembly 1020 and depth scale 1080 may be attached together to form and arc-like assembly. Combined cartridge 1030 may house a slider 2080, lock bar 1040, needle 1070, guidewire 1090, or a combination thereof. While the embodiment shown only illustrates a combined cartridge with a needle, in other embodiments, a second slider coupled to a sheath may be provided or the needle may be substituted with a sheath. Since needle 1070 is coupled to slider 2080, the needle 1070 advances or retracts when the slider 2080 moves forward or backward. When handheld device 1015 is properly positioned over a vessel, an imaging device may be utilized to determine the depth of the vessel. Once the depth of the vessel is determined, the combine cartridge 1030 may be adjusted along the depth scale 1080 until a desired insertion depth is indicated. Next, the combined cartridge may be locked in position and the needle 1070 may be advanced so that the tip reaches the desired insertion depth or so that the tip reaches into the lumen of the vessel. A needle, sheath, and/or guidewire can be removed from combined cartridge 1030 when the insertion process is complete, and the components can be replaced with sterile components for further use in the future. Lock bar 1040 may be utilized to lock the needle slider 2080 in a desired position. For example, when the handheld device 1015 is not in use, it may be desirable to prevent needle 1070 from advancing for safety reasons.

In the embodiment shown, the handheld device 1015 is completely manually operated by a user and does not require electric power to operate. However, in other embodiments, one or more features of the device may be motorized. In one embodiment, movement of combined cartridge 1030 along the depth scale may be motorized. Additionally, a needle, sheath, and/or guidewire provided by combined cartridge 1030 may be motorized. Discussion of motorize operation of handheld devices is provided in U.S. patent application Ser. No. 13/080,348 and U.S. patent application Ser. No. 13/080,370, which are incorporated by reference. In some embodiments, a handheld device may be disposed after a single use, such as the embodiments shown in FIG. 2A. In other embodiments, the handheld device may be suitable for repeated use.

Figure 2B:
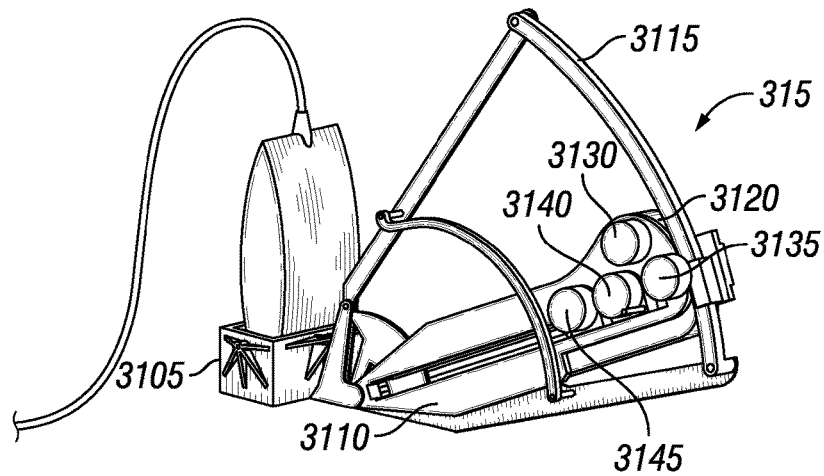
Figure 2C:
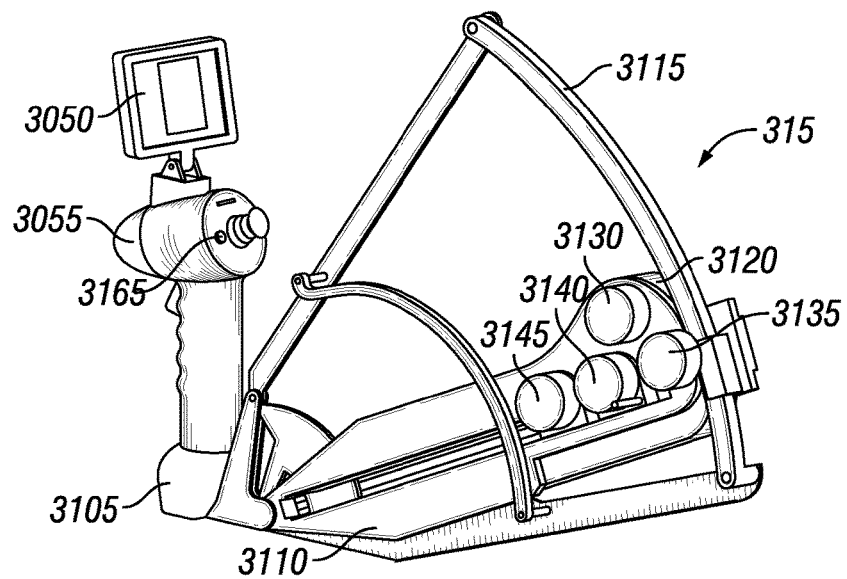

FIGS. 2B and 2C are illustrative implementations of a handheld device with motorized components. In FIG. 2B, an imaging device, such as an ultrasound, can be coupled to handheld device. It should be noted that a preexisting imaging device is utilized and that this preexisting imaging device is not part of handheld device. This arrangement allows any suitable brand or type of existing imaging device to be utilized with handheld device. For example, a preexisting ultrasound transducer may be secured to handheld device in preparation for use of the insertion system, and the transducer may be removed when desired. By utilizing a preexisting imaging device that an operator already owns, the cost of purchasing a new imaging device is avoided and the cost of a handheld device can be reduced significantly. In FIG. 2C the imaging device is incorporate into handheld device to provide a system that does not require any additional parts.

Handheld device 315 may include an imaging device attachment 3105, cartridge carrier 3110, arc arm 3115, cartridge 3120, attachment points 3125, guidewire motor 3130, angle motor 3135, needle motor 3140, sheath motor 3145, guidewire actuator 3150, needle actuator 3155, and sheath actuator 3160. Imaging device attachment 3105 is utilized to secure image capturing instrument of imaging device to handheld device 315. For example, an ultrasound transducer may be placed in imaging device attachment 3105 and secured to handheld device 315. In the embodiment shown in FIG. 2C, the imaging device attachment 3105 incorporates an imaging device into an ergonomic handle, including an ultrasound transducer (not shown) and display 3050. Opposite the side shown, arm 3110 may secure a cartridge or incorporate a cartridge with the arm. For example, a disposable cartridge may be attached to arm 3110 or the needle, sheath, and/or guidewire assembly may be incorporated into arm 3110. A first end of arm 3110 is pivotally attached to handheld device 315 near image device attachment 3105. The opposite end of arm 3110 is coupled to arc arm 3115. Angle motor 3135 on arm 3110 may be coupled to arc arm 3115 as well to adjust the angle of arm 3110. For example, angle motor 3135 may be coupled to a gear or wheel that rotates to adjust the angle of arc arm 3115. Further, arc arm 3115 may include gear teeth that mate with the teeth on the gear or wheel coupled to angle motor 3135. The arm 3110 may provide an indicator so that position of arm 3110 on arc arm 3115 indicates an achievable insertion depth on the depth scale.

Guidewire motor 3130 may be coupled to a guidewire actuator on arm 3110. When a cartridge 3130 with a guidewire is properly attached to arm 3110, guidewire motor 3130 may actuate the guidewire actuator to advance or retract the guidewire. Needle motor 3140 may be coupled to a needle actuator on arm 3110. When a cartridge 3130 with a needle is properly attached to arm 3110, needle motor 3140 may actuate the needle actuator to advance or retract the needle. Sheath motor 3145 is coupled to a sheath actuator on arm 3110. When a cartridge 3130 with a sheath is properly attached to arm 3110, sheath motor 3145 may actuate the sheath actuator to advance or retract the sheath. Guidewire motor 3130, angle motor 3135, needle motor 3140, and sheath motor 3145 may be coupled to a power source. For example, handheld device 315 may attach to a power cable that may be plugged into a power outlet or handheld device 315 may include a rechargeable battery pack 3055.

In order to control the operation of guidewire motor 3130, angle motor 3135, needle motor 3140, and sheath motor 3145, handheld device 315 may provide one or more controllers. The controllers may be buttons, switches, joysticks, thumbsticks, a keypad, a combination thereof, or any other suitable controls. For example, each individual motor may be controlled by a separate controller or by a combined controller that allows an operator to advance and/or retract a guidewire, needle, or sheath. The position of the one or more controllers are placed to allow operation of the device with a single hand. Further, a controller may operate a motor utilized to adjust the angle of arm 3110. In the embodiment shown in FIG. 2C, a button and thumb stick 3165 utilized to operate the device are shown. Guidewire motor 3130 may have a corresponding guidewire controller. Angle motor 3135 may have a corresponding angle/depth controller. Needle motor 3140 may have a corresponding needle controller. Sheath motor 3145 may have a corresponding sheath controller. Guidewire, needle, and sheath controllers may allow an operator to advance or retract the component, whereas angle/depth controller may allow the operator to adjust the angle of arc 3110 to adjust for a targeted insertion depth. In some implementations, an operator may operate the controller to adjust the angle of arm 3110 to a desired target depth shown on a depth scale. In other implementations, an operator simply enters a desired target depth into the controller or the target depth is indicated by selecting a target vessel, which causes handheld device 315 to automatically adjust the angle of arm 3110 to achieve the targeted depth. In another embodiment, a single motor may utilized to provide the functionality of guidewire motor 3130, angle motor 3135, needle motor 3140, and sheath motor 3145. The single motor may be connected to a gear case that is capable of switching between modes that allow the single motor to control the guidewire, needle, sheath, and the angle of arm 3110.

Figure 2D:
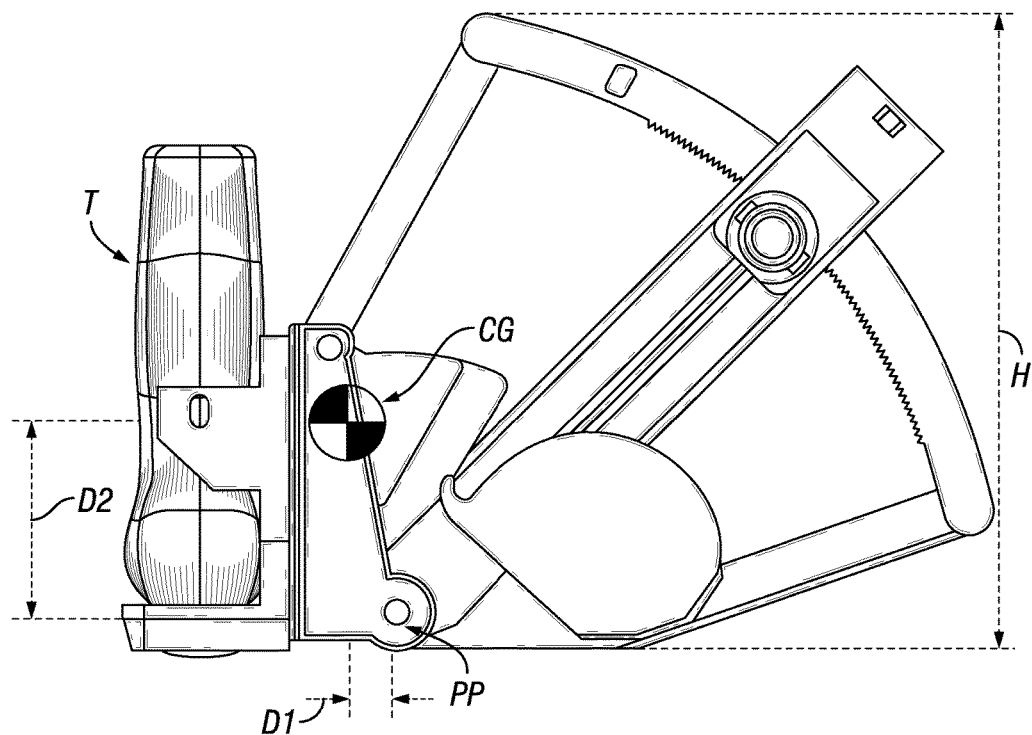
Figure 2E:
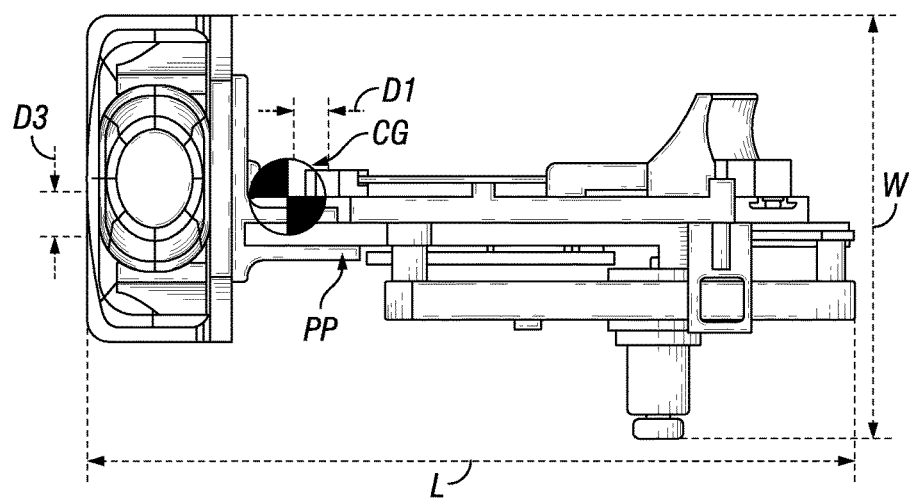

FIGS. 2D-2E are an example illustrating the position of the center of gravity (CG) for a handheld device. While the embodiment shown in FIGS. 2D-2E illustrates a manually operated handheld device, it will be recognized by one of ordinary skill in the art that other embodiments of handheld devices discussed herein (e.g. embodiments providing motorized operation, embodiments incorporating the imaging device, or the like) may have or may be modified to provide the CG features discussed herein. The various embodiments of handheld devices discussed herein are designed for ease of operation. In the various embodiments discussed herein, handheld devices have been designed to provide a center of gravity near or at a pivot point (PP) of the pivotal arm. By centralizing the weight of the device near area where the handheld device is held, the device can easily be handled with one hand. In embodiments that do not provide a handle, the handheld device may be held by an attached transducer. FIG. 2D shows a side view of the handheld device and FIG. 2E shows a top view of the handheld device. The y-axis represents the vertical axis along the height (h) of the handheld device, the x-axis represents an axis along the length (l) of the handheld device, and the z-axis represents an axis along the width (w) of the handheld device. The CG is adjacent to location where the handheld device is held by an operator or near transducer (T). While a transducer is shown, in other embodiments with an imaging device incorporated into a handle, the handle will be present where the transducer is shown. Further, the CG is adjacent to PP of the arm of the handheld device. The CG is adjacent to a midpoint of the total width of the handheld device. The CG is below a midpoint of the total height of the handheld device. In some embodiments, the distance between the PP and CG on the x-axis (D1) is equal to or less than 10 mm. In some embodiments, the distance between the PP and CG on the y-axis (D2) is equal to or less than 37 mm. In some embodiments, the distance between the PP and CG on the z-axis (D3) is equal to or less than 8 mm. As shown in the embodiments of FIGS. 2A-2C, a main body of the device provides an arc-like structure. The imaging device attachment or handle with an imaging device incorporated is positioned at or near the center of the arc-like structure. This allows the weight of the imaging device to be positioned at or near the location where the device is handled by a user. Additionally, the arc-like structure is designed to have a weight distribution that is balanced. Weight is centralized on a plane of the arc-like structure so that it does not easily tip over to the left or right. The weight is also focused low and as close to where the device is handled by the user. Further, the pivotal arm is positioned at or near the center of the arc-like structure so that the weight of the pivotal arm is as close as possible to where the device is handled. As noted previously, some embodiments may provide motorized adjustment of the arm and motorized movement of a needle, sheath, and/or guidewire. Such embodiments allow the device to be handled and/or operated easily with a single hand throughout the entire insertion process.

Figure 3A:
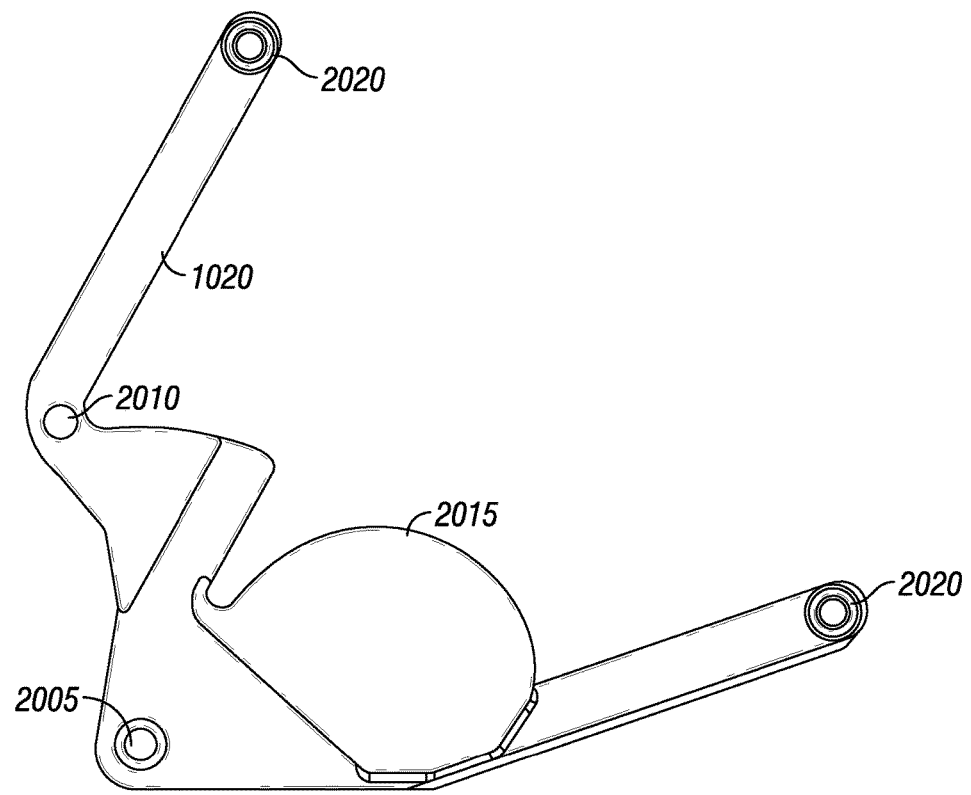
FIGS. 3A-3B are illustrative implementations of a frame assembly and slide stop.
Figure 3B:
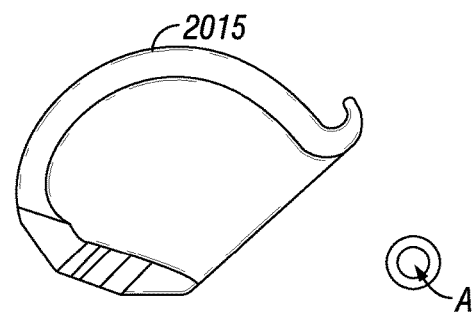
Figure 3D:
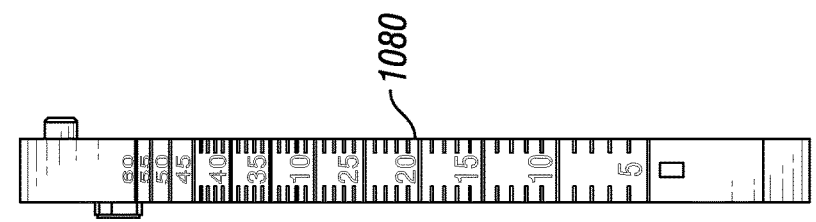
FIGS. 3C-3D are illustrative implementations of a depth scale.
Figure 3C:
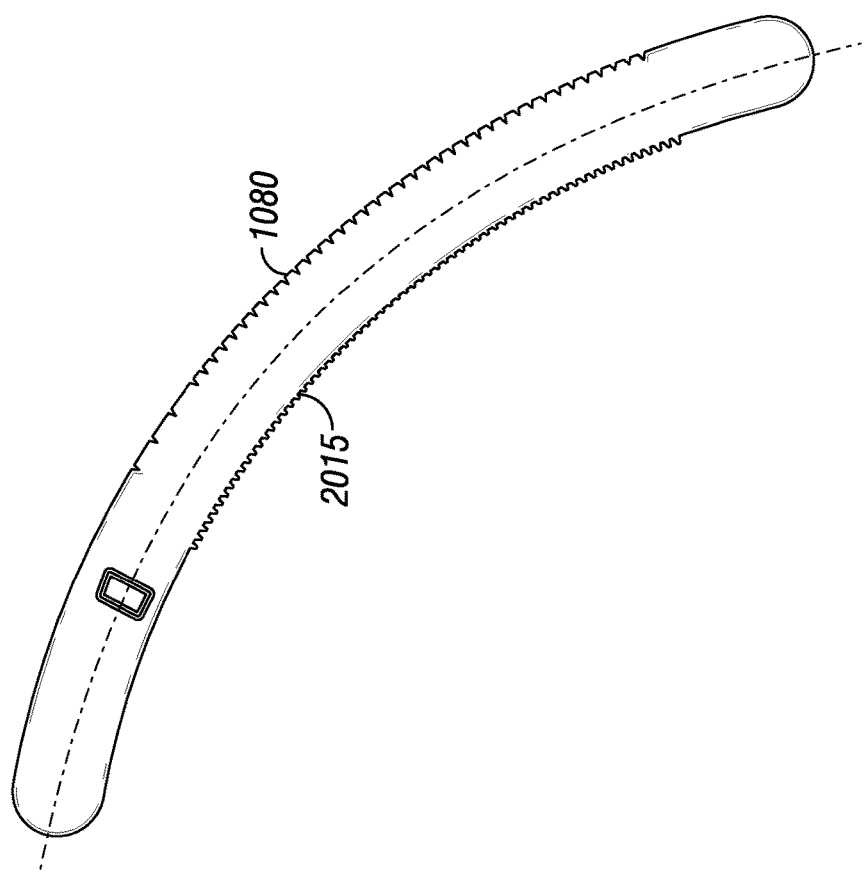

FIG. 3A is an illustrative exemplary embodiments of frame assembly 1020. Frame assembly 1020 provides an opening 2005 that may be utilized to pivotally attach combined cartridge 1030. In some embodiments, opening 2010 and opening 2005 may be utilized to attach a transducer mount to frame assembly 1020. Attachment points 2020 are utilized to attach the depth scale 1080 to the frame assembly 1020. FIG. 3B is an illustrative exemplary embodiment of a frame assembly slide stop 2015. Slide stop 2015 prevents a needle slider from advancing past a desired distance to prevent the needle from advancing beyond a desired insertion depth. FIG. 3C-3D are views of an illustrative embodiment of a depth scale 1080. The depth scale 1080 may be an arc-like shape. In some embodiments, depth scale 1080 provides teeth 2025 that may be mated to a locking mechanism, gear, or the like provided by combined cartridge 1030.

Figure 4A:
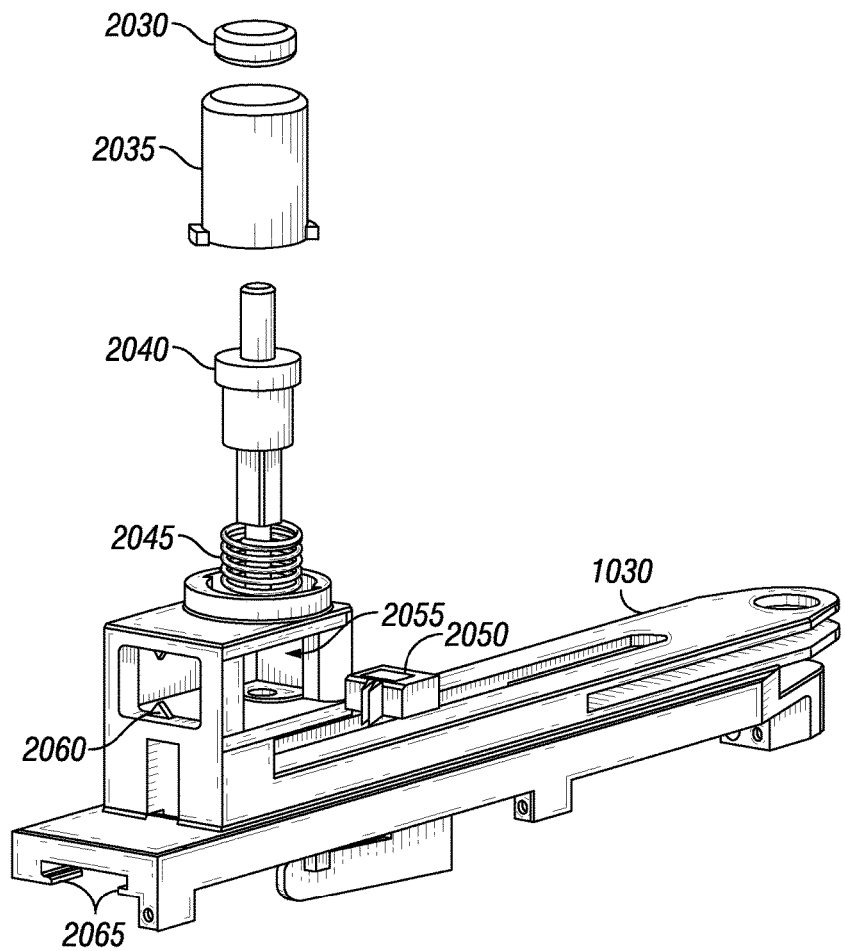
FIGS. 4A-4B are illustrative implementations of a combined cartridge.

FIG. 4A is an illustrative exemplary embodiment of a locking mechanism for a combined cartridge 1030. Combined cartridge 1030 provides a locking mechanism for securing the cartridge in a desired position on the depth scale 1080. A non-limiting exemplary embodiment of a locking mechanism may include a button 2030, housing 2035, shaft 2040, spring 2045 and lock 2050. Opening 2055 in the combined cartridge 1030 may receive the depth scale 1080. When the depth scale 1080 is inserted through opening 2055, indicator 2060 provides a visual indication of the depth setting. Shaft 2040 is placed through an opening in the top of housing 2035 and secured to button 2030. The bottom portion of shaft 2040 is placed through the center of a spring 2045. Housing 2035 may be attached to combined cartridge 1030. Within opening 2055, the bottom portion of shaft 2040 may pass through an opening in lock 2050. Lock 2050 provides teeth or grooves that are suitable for engaging depth scale 1080. Button 2030 is pressed to cause lock 2050 to engage or disengage the depth scale 1080. When engaged, the teeth on lock 2050 engage the teeth 2025 of the depth scale 1080 to lock combined cartridge 1030 in a desired position on the depth scale. To disengage the lock 2050, button 2030 is pressed and causes the teeth on lock 2050 to disengage depth scale 1080. Slider slot 2065 is utilized for the needle slider as discussed in more detail below. While the locking mechanism discussed provides a push button system, any suitable locking mechanism may be provided.

Figure 4B:
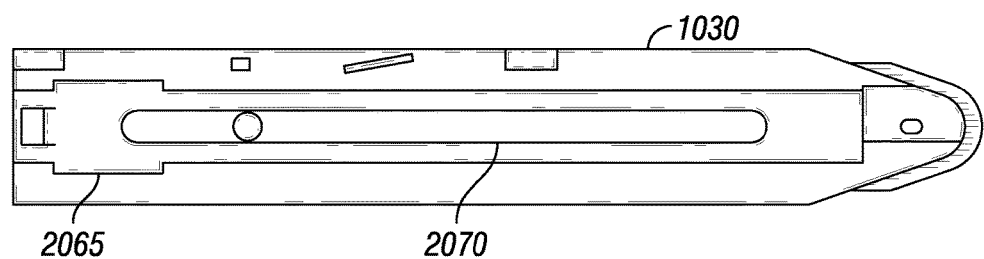

FIG. 4B is an illustrative embodiment of a slider slot for a combined cartridge 1030. Slider slot 2065 provides grooves on combined cartridge 1030 that are utilized couple a slider to the combined cartridge. Slider slot 2065 allows the slider to slide within its grooves along the length of the combined cartridge 1030. Additionally, slot 2070 provides an opening in combined cartridge 1030 that may be utilized to receive a portion of a slider.

FIG. 5A-5B is an illustrative embodiment of a needle slider 2080. Needle slider 2080 provides a needle opening 2085, guides 2090, and stop extension 2095. Needle opening 2085 receives and secures a needle to the needle slider 2080. Guides 2090 fit into the slider slot 2065 of combined cartridge 1030. Guides 2090 allow the needle slider 2080 to slide back and forth within the slider slot 2065 along the length of the combined cartridge 1030. Stop extension 2095 fits through slot 2070 of the combined cartridge 1030 when the needle slider 2080 is attached to the combined cartridge. When the combined cartridge 1030 is secured to the frame assembly 1020, stop extension 2095 may engage the slide stop 2015 when the needle slider 2080 is moved towards the transducer mount 1050. As the combined cartridge 1030 is pivoted about frame assembly 1020, a depth indicated on the depth scale 1080 changes. The shape of the slide stop 2015 allows a distance that the needle slider 2080 can be advanced before contacting the slide stop 2015 to be controlled in accordance with the position of the combined cartridge 1030 on the frame assembly 1020 and depth scale 1080. While the slider discussed above is utilized for a needle, it will be recognized by one of ordinary skill in the art that the slider can be adapted to be utilized for a sheath, such as by adapting opening 2085 to be suitable for securing a sheath.

FIGS. 6A-6B are an illustrative exemplary embodiment of a transducer mount 1050. Openings 3005 may be utilized to secure the transducer mount 1050 to frame assembly 1020. For example, openings 3005 may be matched up with openings 2005, 2010 in frame assembly 1020. Further, dowels, pins, or the like may be placed through the openings 2005, 2010, 3005 to secure the transducer mount 1050 to the frame assembly 1020. Transducer mount 1050 may provide slots 3010 that may be utilized to secure the transducer adapter 1060 to the transducer mount. For example, transducer adapter 1060 may provide protrusion that fit into slots 3010. When the transducer adapter 1060 rotated the protrusions lock into slots 3010 to secure the transducer adapter to the transducer mount 1050. While the embodiment shown utilizes a twist lock mechanism for securing the transducer adapter 1060 to the transducer mount 1050, any suitable attachment mechanism may be utilized.

FIGS. 7A-7B provide an illustrative embodiment of handheld device 1015 in an assembled view and a disassembled view. Handheld device 1015 provide a frame assembly 1020, combined cartridge 1030, transducer mount 1050, transducer adapter (not shown), depth scale 1080, and slide stop 2015. A first end of a combined cartridge 1030 is pivotally attached to frame assembly 1020 at a fixed position. A second end of the combine cartridge 1030 is engaged with depth scale 1080 so that the combined cartridge moves along an arc-like path of the depth scale when it is pivotally rotated. Depth scale 1080 is attached to arms of the frame assembly 1020 extending away from pivot attachment point for the combined cartridge 1030. Combined cartridge 1030 may be moved along depth scale 1080 to adjust a needle insertion depth, which is indicated by the depth scale. When handheld device 1015 is adjusted to a desired insertion depth, button 2030 of a locking mechanism may be actuated to lock the combined cartridge 1030 in a desired position. Needle slider 2080 may be advance along the length of the combined cartridge 1030 until the needle slide engages slide stop 2015. When needle slide 2080 engages slide stop 2015, a needle tip has been advanced to the desired insertion depth. While the embodiment shown provides a needle slider 2080, in other embodiments it may be desirable to also include a sheath slider or substitute the needle slider with a sheath slider.

In other embodiments, a pivot point of the combined cartridge 1030 may be slideably attached to the frame assembly 1020. In some embodiments, a transducer mount 1050 may be coupled to frame assembly 1020 to facilitate mounting of the transducer adapter 1060. In other embodiments, the frame assembly 1020 may incorporate a transducer mount that allows the transducer adapter 1060 to be directly attached to the frame assembly 1020. Transducer adapter 1060 may have a variety of different shapes or arrangements to accommodate different types and/or brands of transducers.

Figure 8A:
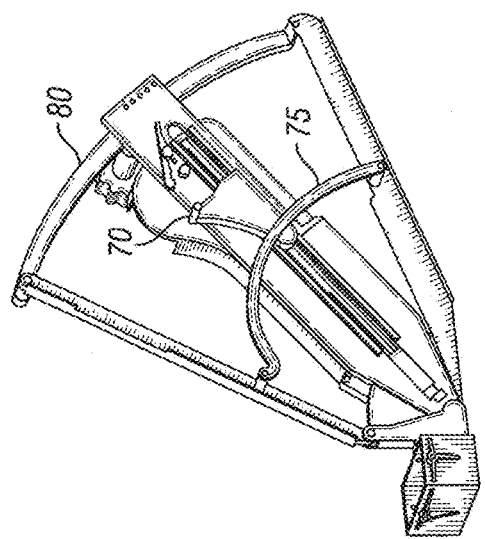
FIGS. 8A-8B are illustrative implementations of a reusable handheld device with a disposable cartridge.
Figure 8B:
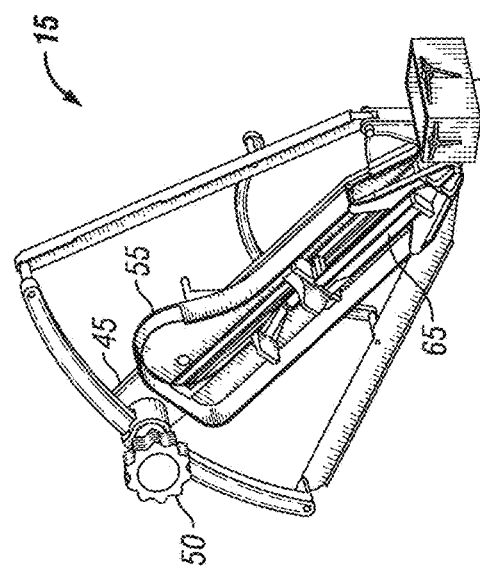

FIGS. 8A and 8B are illustrative implementations of a reusable handheld device 15. For the purposes of illustration and clarity, reusable handheld device 15 is shown without an imaging device and sterile cover. An imaging device, such as an ultrasound, can be coupled to reusable handheld device 15, but the imaging device is not a part of the reusable handheld device and may be removed when desired. This arrangement allows any suitable brand or type of imaging device to be utilized with handheld device 15.

Reusable handheld device 15 may include an articulating arm 45, thumb wheel 50, cartridge 55, imaging device attachment 60, removable lock bar, 65, slider stop bar 70, slide stop 75, and depth adjustment scale 80. Imaging device attachment 60 is utilized to secure the image capturing instrument of an imaging device to reusable handheld device 15. For example, an ultrasound transducer may be placed in imaging device attachment 60 and secured to reusable handheld device 15. Reusable handheld device 15 may provide attachment points to hold and support cartridge 55 on articulating arm 45. For example, cartridge 55 may be an alignment cartridge or cartridge. Reusable handheld device 15 also includes a thumb wheel 50 that changes the angle of articulating arm 45.

Removable lock bar 65 locks sliding mechanisms on cartridge 55 in place and may be place onto cartridge 55 to prevent inadvertent advancement or insertion of a needle, catheter, and/or the like. Slider stop bar 70 on cartridge 55 slides in the direction of slide stop 75 when a needle slider or needle is advanced. Slider stop bar 70 impedes advancement of the needle when it comes into contact with slide stop 75, thereby preventing a medical practitioner from over advancing a needle past a target vessel. Reusable handheld device 15 may also include a depth adjustment scale 80. When a desired depth is determined using an imaging device, thumb wheel 50 and depth adjustment scale 80 may be utilized to adjust articulating arm 45 to the correct angle for reaching the desired depth.

Figure 9A:
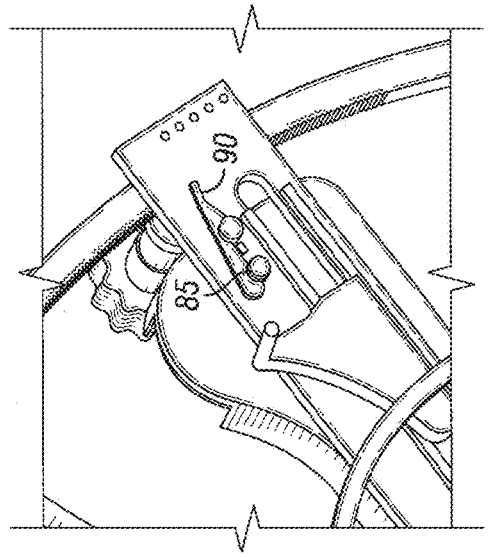
FIGS. 9A-9B are illustrative implementations of close up views of a reusable handheld device with a disposable cartridge.
Figure 9B:
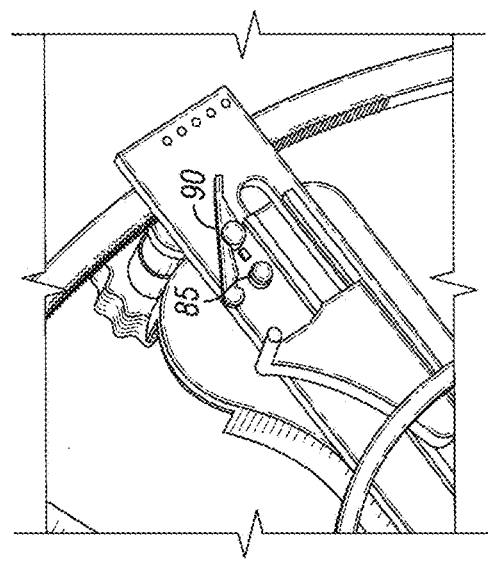

FIGS. 9A and 9B are illustrative implementations of a reusable handheld device 15 and cartridge 55. When cartridge 55 is mated correctly to reusable handheld device 15, locking pin 85 protruding from the bottom of cartridge 55 extends through articulating arm 45 of reusable handheld device 15. Articulating arm 45 provides locking arm 90 for securing cartridge 55 to reusable handheld device 15. For example, locking pin 85 may provide a groove that locking arm 90 may be place into for securing cartridge 55. While locking pin 85 and locking arm 90 are provided in the figure shown, it should be recognized by one of ordinary skill in the art that any suitable securing means may be substituted.

Figure 10A:
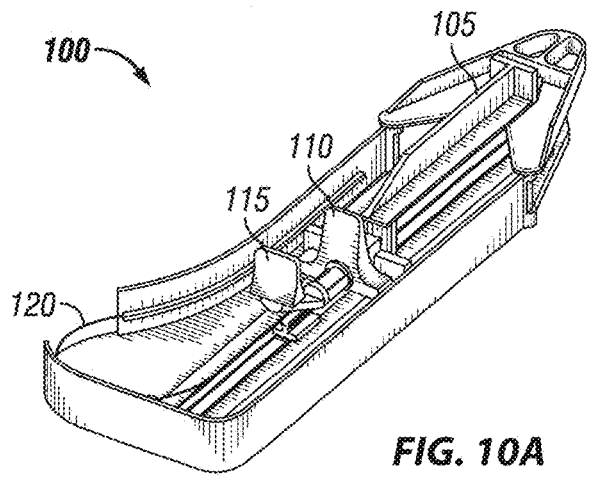
FIGS. 10A and 10B are illustrative implementations of a cartridge.
Figure 10B:
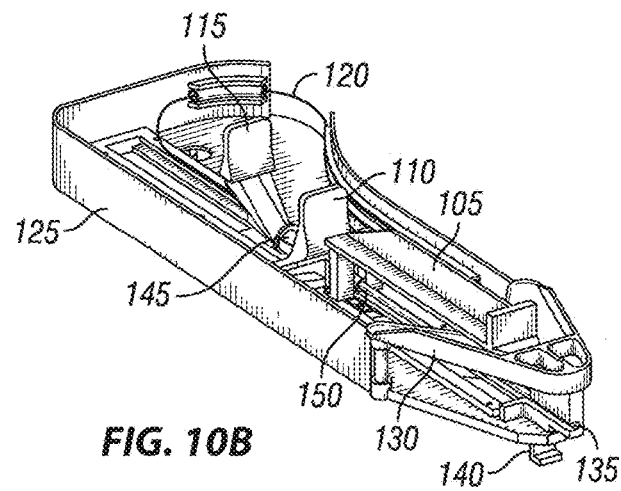

FIGS. 10A and 10B are illustrative implementations of a cartridge 100. Cartridge 100 is sterile to prevent the spread of bacteria, disease, etc. Cartridge 100 may be disposed after a single use. Cartridge 100 may include lock bar 105, sheath slider 110, needle slider 115, guidewire 120, cartridge base 125, span brace 130, guide slot 135, and attachment tab 140. Attachment tab 140 is an L-shaped tab that may be secured to the reusable handheld device. A locking pin and attachment tab 140 mates cartridge 100 to the reusable handheld device.

Lock bar 105 is designed to secure the sheath slider 110, needle slider 115, and/or associated medical components in a desired position to prevent undesired movement before lock bar 105 is removed. For example, during shipping, before attachment to the reusable handheld device, and/or prior to use it is desirable to prevent a sharp needle and sheath from protruding from cartridge 100. However, when cartridge 100 is attached to a reusable handheld device that is ready for use, lock bar 105 may be removed to allow sheath slider 110, needle slider 115, and associated medical components to be freely advanced and retracted.

Cartridge 100 may also include a sterile needle 145, sheath 150, and guidewire 120. Guidewire 120 runs inside a track located in the wall of cartridge 100 and continues through the inside of needle 145. Needle 145 is positioned in the center of sheath 150 and may slide into and out of sheath 150. In some implementations, a dilator may be provide in between needle 145 and sheath 150 to minimize or prevent bending of needle 145. There are two sliders in cartridge 100. Needle slider 115 controls the advancement and retraction of the needle 145. Needle slider 115 is coupled to slider stop bar 70 shown in FIG. 8B. As needle slider 115 is advanced, slider stop bar 70 is also advanced. The depth the tip of needle 145 extends from reusable handheld device 15 is determined by rotating thumb wheel 50 until depth adjustment scale 80 on reusable handheld device 15 shows the desired depth. Pushing needle slider 115, toward a patient until the slider stop bar 70 hits slide stop 75, causes needle 145 to extend out from cartridge 100 and into a patient to the desired depth. Moving needle slider 115 away from the patient until it hits the proximal end of a slider track fully retracts needle 145 into cartridge 100.

Sheath slider 110 controls the advancement and retraction of sheath 150. Because sheath slider 110 is placed in front of needle slider 115, advancing needle slider 115 also causes sheath slider 110 to advance. However, retracting of needle slider 115 does not cause sheath slider 110 to retract. Additionally, sheath slider 110 is not coupled to slider stop bar 70, which allows sheath slider 110 to be advanced further than needle slider 115. Sheath 150 has a larger diameter than needle 145 and is placed over the needle. Guidewire 120 passes through needle 145. Pushing sheath slider 110 toward the patient advances sheath 150 over needle 145 tracking over guidewire 120 and into a target vessel. Guide slot 135 supports needle 145 during insertion. Guide slot 135 does not completely surround needle 145 or sheath 150 so as to provide an exit point for the sheath 150 after it has been inserted into the patient. Cartridge 100 may provide an opening below span brace 130 that allows sheath 150 to be easily removal of from cartridge 100.

Figure 11:
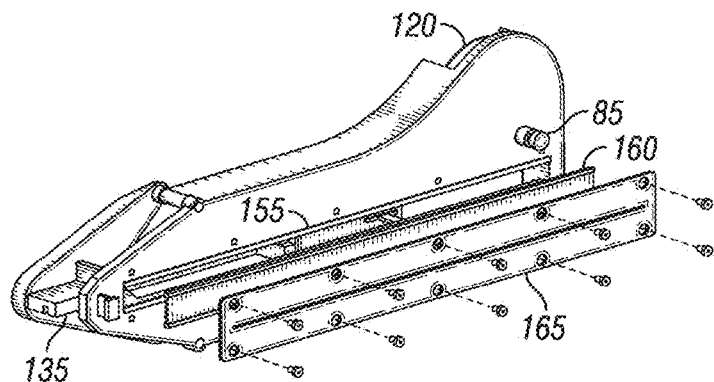
FIG. 11 is an illustrative implementation of a back portion of a cartridge.

FIG. 11 is an illustrative implementation of a back portion of a cartridge 100. Both the needle and sheath sliders run along slider track 155. A seal 160 may be place on slider track 155 to maintain a seal around a slider as it moves along slider track 155. Slider track plate 165 is place over seal 160 and may be secured to cartridge 100. Cartridge 100 may also include a sterile cover attached to the cartridge via slider track plate 165 or any other suitable attachment point. The cover can be positioned over an image capturing instrument and the reusable handheld device when cartridge 100 is attached to the reusable handheld device 15. This sterile cover is not shown in the figures above to provide an unobstructed view of the cartridge features. Guidewire 120 is advanced by grasping the guidewire with the forefinger and thumb and moving it in a proximal direction. This will cause guidewire 120 to advance in the distal direction through the needle into the patient's vessel. During advancement of guidewire 120, the operator may view the advancement of guidewire 120 on a display of the imaging device. Guidewire 120 may also be advanced by grasping the guidewire proximal to the needle hub and moving the guidewire through the needle into the patient's vessel.

Figure 12:
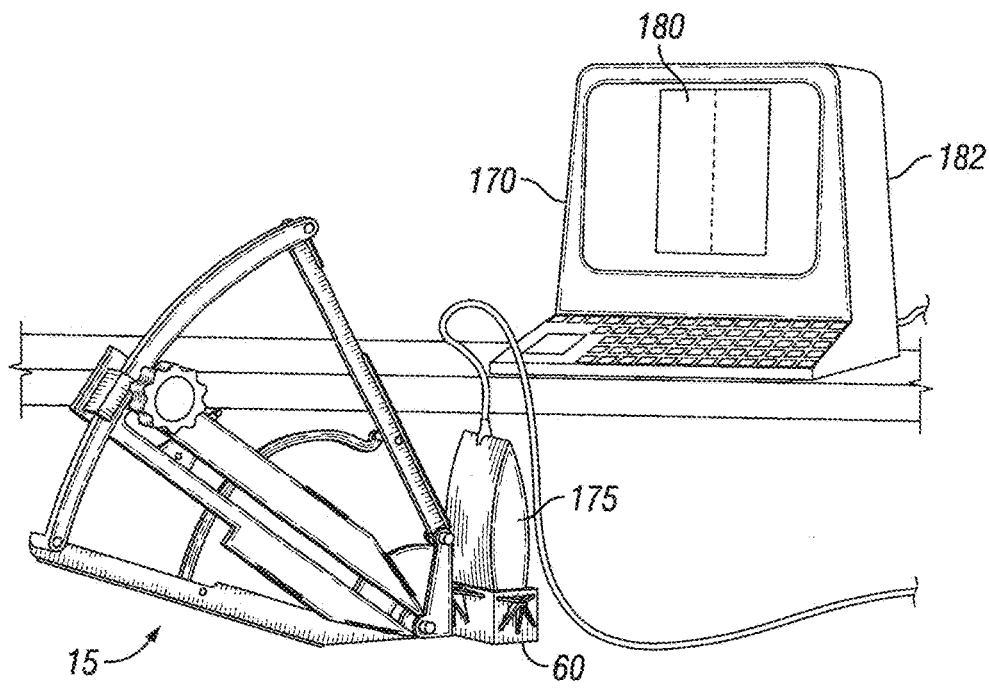
FIG. 12 is an illustrative implementation of a reusable handheld device and imaging device.

FIG. 12 is an illustrative implementation of a reusable handheld device 15 and imaging device 170. Imaging device 170 may include an image capturing instrument 175 that may be secured in imaging device attachment 60 of reusable handheld device 15. Image capturing instrument 175 may send and/or received signals utilized to generate images. Imaging device 170 receives data from image capturing instrument 175 and shows the generated images on display 182. For example, a commercially available ultrasound imaging device may be utilized and the ultrasound transducer may be secured in imaging device attachment 60 of the reusable handheld device 15. Screen overlay 180 is a transparent adhesive film that may include a vertical dashed line in the center and tick marks on each side. Screen overlay 180 is designed to fit on and adhere to a display 182 of imaging device 170. Screen overlay 180 provides an operational reference for use of insertion system 10. As discuss previously, some embodiments may integrate the display and image capturing instrument of an imaging device into the reusable handheld device. Further, the screen overlay may be placed on the incorporated display or provided by the incorporated display.

Figure 13:
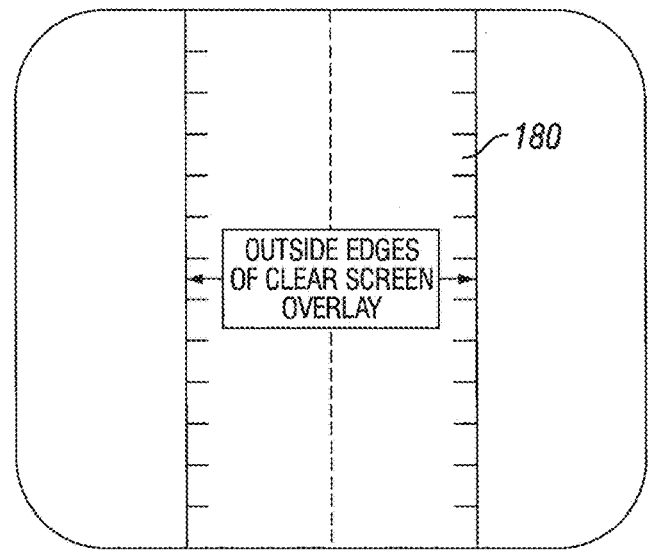
FIG. 13 is an illustrative implementation of a screen overlay.

FIG. 13 is an illustrative implementation of a screen overlay 180. Screen overlay 180 may be a clear, thin, plastic sheet with low tack adhesive that can be affixed to a display 182 of imaging device 170. Screen overlay 180 may provide a vertical dashed center line and tick marks on each side that provides a visual reference aid to the user. Screen overlay 180 and imaging device 170 allow the medical practitioner to accurately locate a vessel and determine the depth of the vessel. The medical practitioner may then set insertion system 10 to the measured depth via hand control of thumb wheel 50 and insert the needle 145, sheath 150, and/or guidewire 120 via hand control of the needle slider 115, sheath slider 110, and/or guidewire 120. It should be noted that an image capturing instrument 175 of the imaging device 170 connects to the reusable handheld device, but imaging device 170 is not part of the insertion system. Since medical facilities may already have a suitable preexisting imaging device, utilizing a preexisting imaging device, rather than incorporating a new imaging device, reduces cost. For example, a preexisting ultrasound obtained previously by a hospital, doctor, or the like may be utilized with the reusable handheld device, thereby obviating the need to purchase a new imaging device. As such, the reusable handheld device allows the preexisting imaging device to be easily secured to the device and separated from the device. This also allows the sheath insertion methods and systems discussed herein to easily be adapted for use with a variety of different types and/or brands of imaging devices. Imaging devices that are suitable for use with the insertion systems discussed herein will preferably be capable of imaging and measuring depths of approximately 5 mm to 60 mm. While embodiments discussed above illustrate usage with reusable handheld device 15, it will be recognized by one of ordinary skill in the art that imaging as discussed above can be similarly applied to any handheld device, such as the various embodiments of handheld devices in FIGS. 2A-2C.

Figure 14:
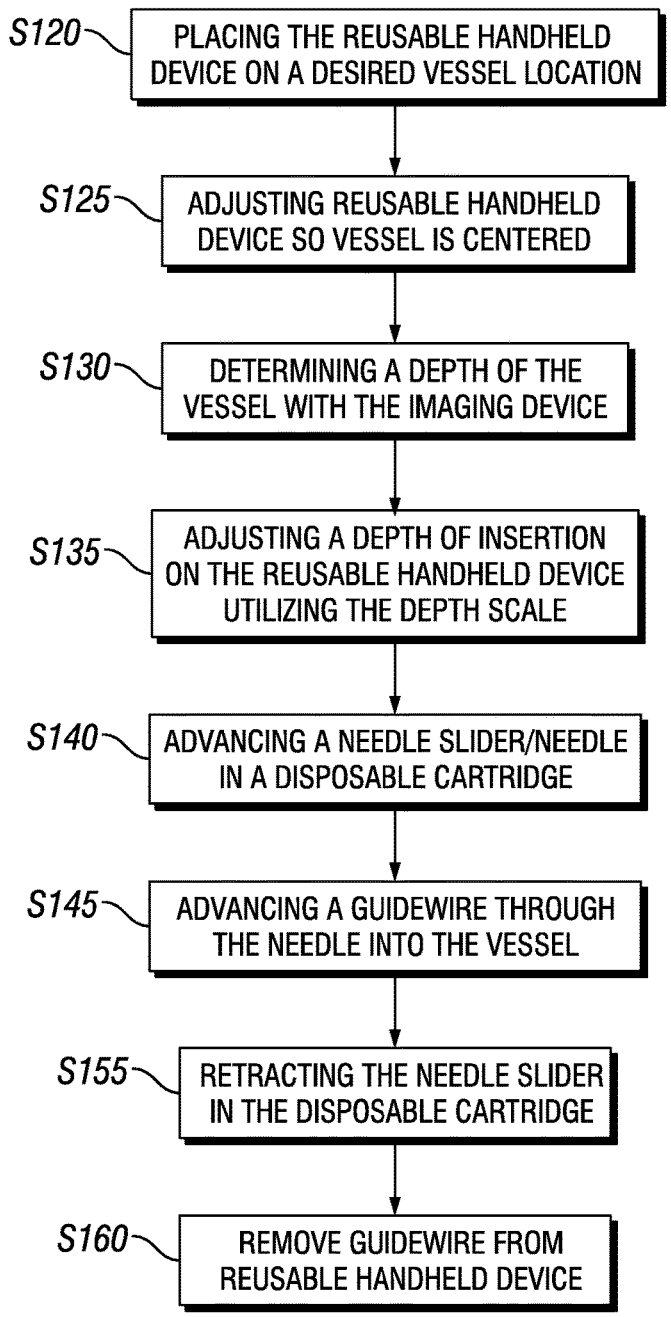
FIG. 14 is an illustrative implementation of a method for inserting a sheath into a vessel.

FIG. 14 is an illustrative implementation of a method for inserting a needle into a vessel to place a guidewire in the lumen of a vessel. There may be additional steps in a medical procedure after placement of a guidewire. However, medical professionals may have different preferences on the numerous sheath, catheter, or introducer options. As such, after placement of the guidewire, the medical professional is free to select according to their personal preference. While the following provides a description of inserting a needle into a vessel to place a guidewire, it will be recognized by one of ordinary skill in the art that the device is suitable for a variety of medical procedures involving the insertion of a sheath, needle, and/or guidewire into the lumen of a vessel. The scope of the claims is in no way limited to inserting a needle into a vessel, except where expressly stated in the claims. For example, in other implementations, the insertion system may be utilized to place a sheath in the lumen of a vessel or to place a guidewire in the lumen of a vessel with the aid of a needle. While the following method is discussed in regards to handheld device 1015, it will be recognized by one of ordinary skill in the art that the method or variations on the method may be applied to other similar handheld devices, such as reusable handheld device 15, motorize handheld devices, or robotic handheld devices.

Handheld device 1015 can be placed on a desired vessel location to find a target vessel in step S120. The display of the imaging device will provide an image of desired location. In step S125, the operator may adjust handheld device 1015 so the target vessel is centered on the vertical dotted line of screen overlay 180. The operator may then utilize the imaging device 170 to determine the target depth of the vessel in step S130. The target depth indicates the distance from the top surface (or skin of the patient) to the center of the vessel. When the target depth of the vessel is determined, the operator can adjust the combined cartridge 1030 and arm of handheld device 1015 to modify the insertion depth of the needle 1070 utilizing the depth scale 1080 on handheld device 1015 in step S135. In some embodiments, the adjustment of handheld device 1015 may be motorized. Further, some embodiments may provide automatic adjustment that is initiated by actuating a controller, button, trigger or the like. When the combined cartridge 1030 is adjusted to achieve a desired insertion depth, button 2030 can be actuated to lock the combined cartridge in the desired position. Once the operator has modified the insertion depth to the target depth, the needle slider 2080 can be advanced to insert the needle 1070 into the patient in step S140. In some embodiments, the needle may be motorized and advancement may be initiated by actuating a controller, button, trigger or the like. Once the needle 1070 is fully advanced, the operator can advance the guidewire 1090 through the needle into the target vessel in step S145. In some embodiments, the guidewire may be motorized and advancement may be initiated by actuating a controller, button, trigger or the like. Once the guidewire 1090 is advanced into the vessel, the needle 1070 can be retracted in step S155. Finally, in step S160, the guidewire 1090 can be removed from handheld device 1015, thereby completing placement of the guidewire 1090 in the target vessel. This leaves a first end of guidewire 1090 in the lumen of a vessel, and the opposite end outside of a patient's body. While steps involving the handheld device 1015 are completed upon placement of the guidewire 1090 in the target vessel, the medical procedure may require additional steps to be performed.

Figure 15A:
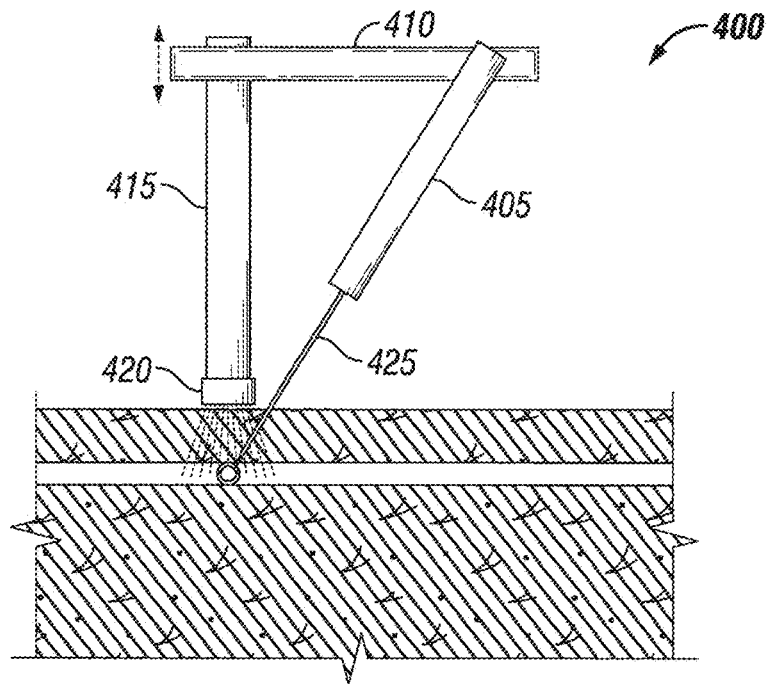
FIGS. 15A-15B are illustrative implementations of a second arrangement for an insertion system.
Figure 15B:
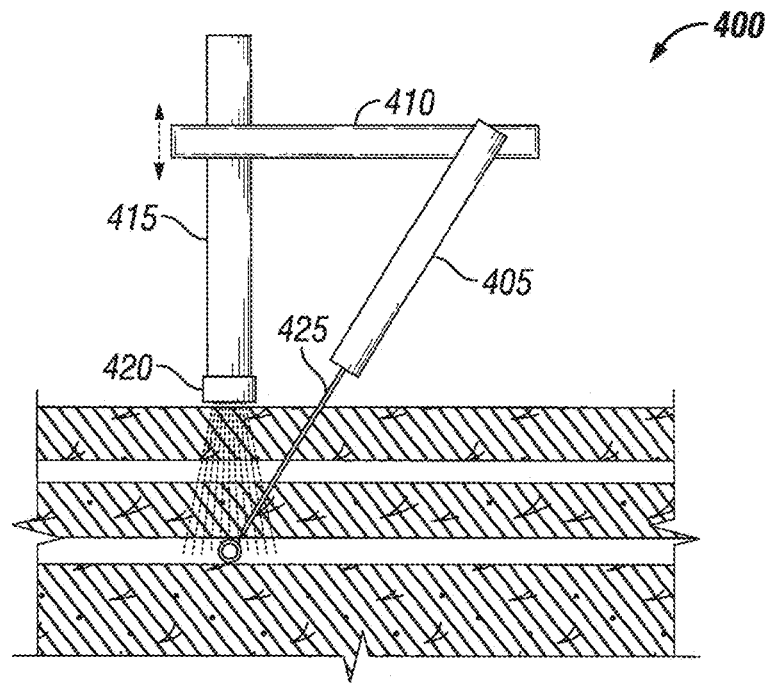

FIGS. 15A and 15B are illustrative implementations of a second arrangement for an insertion system 400. In insertion system 400, cartridge 405 is fixed at a predetermine angle. While cartridge 405 is shown independently attached to boom 410, in other implementations, cartridge 405 may be secured to fixed arm in a similar manner as to the articulating arm 45 shown in FIGS. 9A and 9B. Cartridge 405 may be coupled to adjustable boom 410, which may be adjusted vertically to achieve different target depths. Boom 410 is coupled to transducer arm 415. Transducer arm 415 may provide a depth scale that indicates the needle depths of the range of heights for boom 410. Transducer arm 415 provides an attachment for transducer 420. Needle 425 extends to a fixed predetermined length.

Figure 16A:
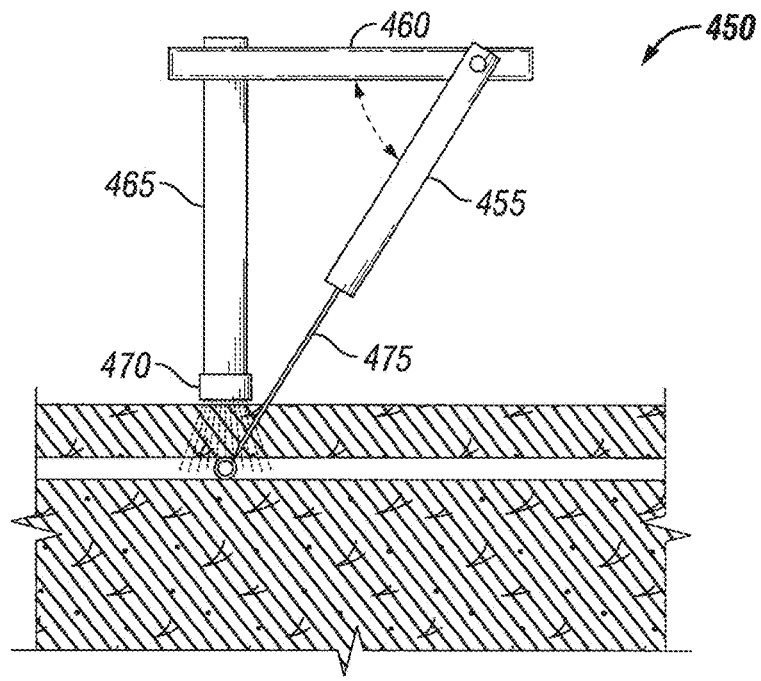
FIGS. 16A-16B are illustrative implementations of a third arrangement for an insertion system.
Figure 16B:
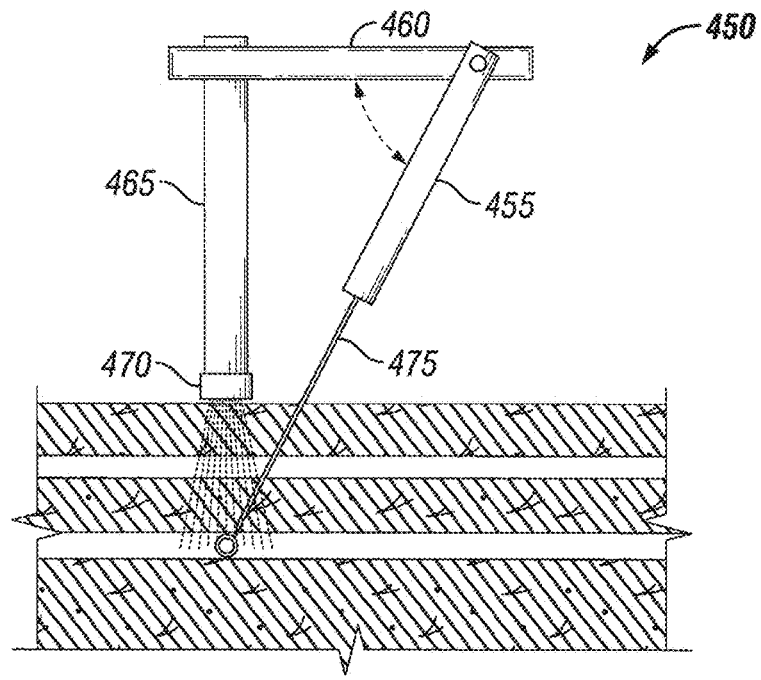

FIGS. 16A and 16B are illustrative implementations of a third arrangement for an insertion system 450. In insertion system 450, cartridge 455 has a variable angle in relation to boom 460. While cartridge 455 is shown independently attached to boom 460, in other implementations, cartridge 455 may be secured to fixed arm in a similar manner as to the articulating arm 45 shown in FIGS. 9A and 9B. In contrast to the previous implementation, boom 460 is a fixed height. Boom 460 is coupled to transducer arm 465, which provides an attachment for transducer 470. Needle 475 is a variable length needle. As the angle of cartridge 455 increase, the depth of insertion increases. The angle of cartridge 455 and length of needle 475 are adjusted to achieve a desired target depth. A depth scale (not shown) for insertion system 450 takes into account the angle of cartridge 455. The depth scale may indicate the depth of needle 475 based on the angle of cartridge 455 and the amount needle 475 has been extended.

Figure 17A:
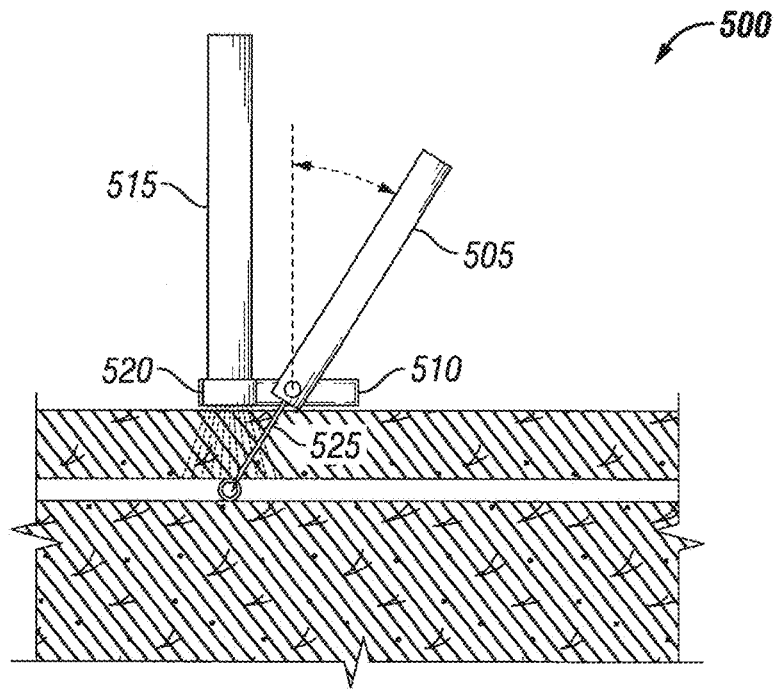
FIGS. 17A-17B are illustrative implementations of a fourth arrangement for an insertion system.
Figure 17B:
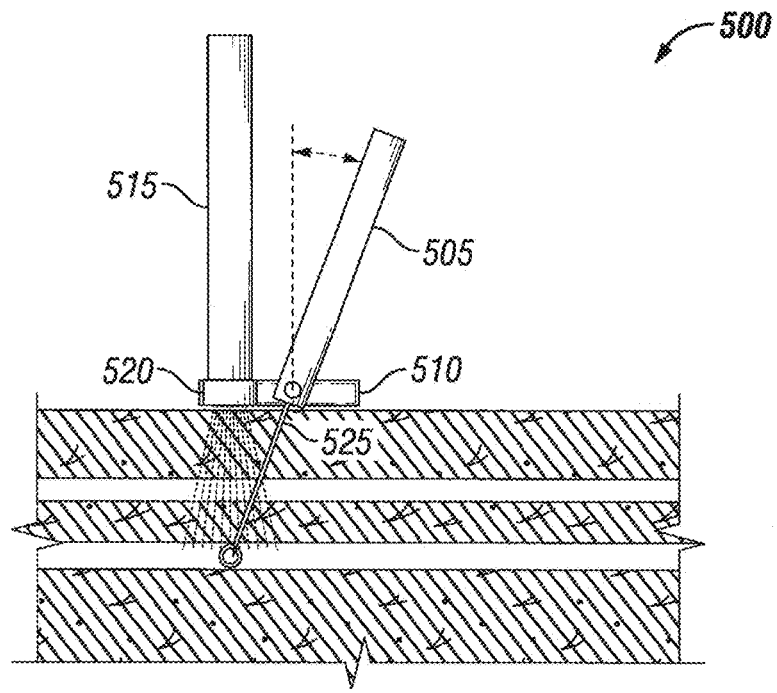

FIGS. 17A and 17B are illustrative implementations of a fourth arrangement for an insertion system 500. In insertion system 500, cartridge 505 has a variable angle in relation to boom 510. While cartridge 505 is shown independently attached to boom 510, in other implementations, cartridge 505 may be secured to fixed arm in a similar manner as to the articulating arm 45 shown in FIGS. 9A and 9B. Boom 510 is fixed near the bottom of transducer arm 515. Transducer arm 515 provides an attachment for transducer 520. Needle 525 is a variable length needle. As in the previous implementation, the angle of cartridge 505 and length of needle 525 are adjusted to achieve a desired target depth. A depth scale (not shown) for insertion system 500 takes into account the angle of cartridge 505. The depth scale may indicate the depth of needle 525 based on the angle of cartridge 505 and the amount needle 525 has been extended.

Figure 18A:
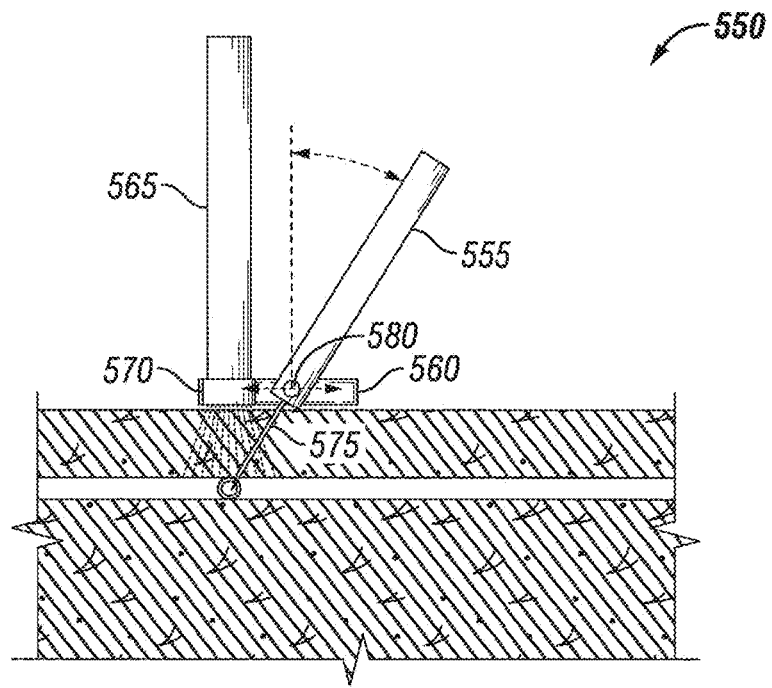
FIGS. 18A-18B are illustrative implementations of a fifth arrangement for an insertion system.
Figure 18B:
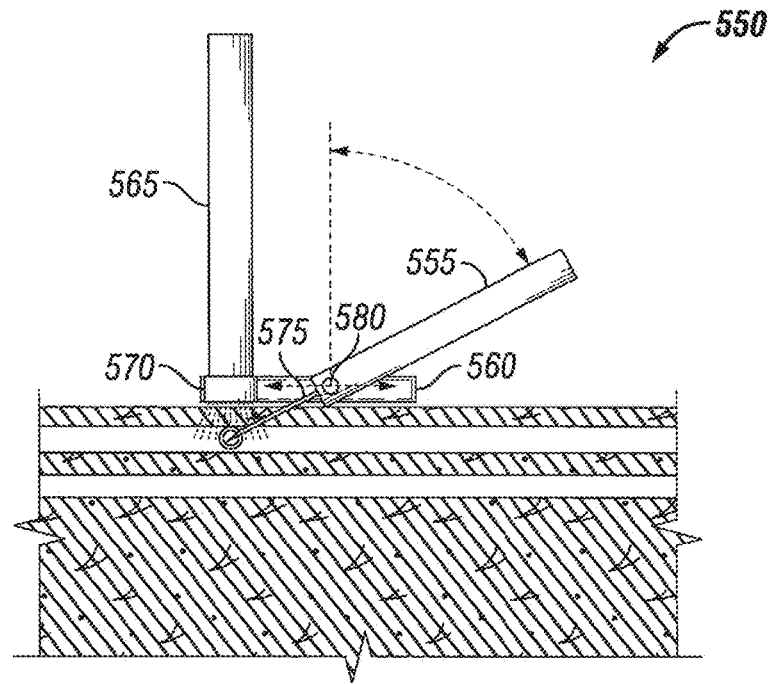

FIGS. 18A and 18B are illustrative implementations of a fifth arrangement for an insertion system 550. In insertion system 550, cartridge 555 has a variable angle in relation to boom 560. While cartridge 555 is shown independently attached to boom 560, in other implementations, cartridge 555 may be secured to fixed arm in a similar manner as to the articulating arm 45 shown in FIGS. 93A and 9B. Boom 560 is fixed near the bottom of transducer arm 565. Transducer arm 565 provides an attachment for transducer 570. Needle 575 is a fixed length needle. In contrast to the previous implementations, cartridge 555 has a variable pivot point 580 that can be moved along boom 560. The angle of cartridge 555 and variable pivot point 580 are adjusted to achieve a desired target depth. A depth scale (not shown) for insertion system 550 takes into account the angle of cartridge 555 and the variable pivot point 580.

Figure 19A:
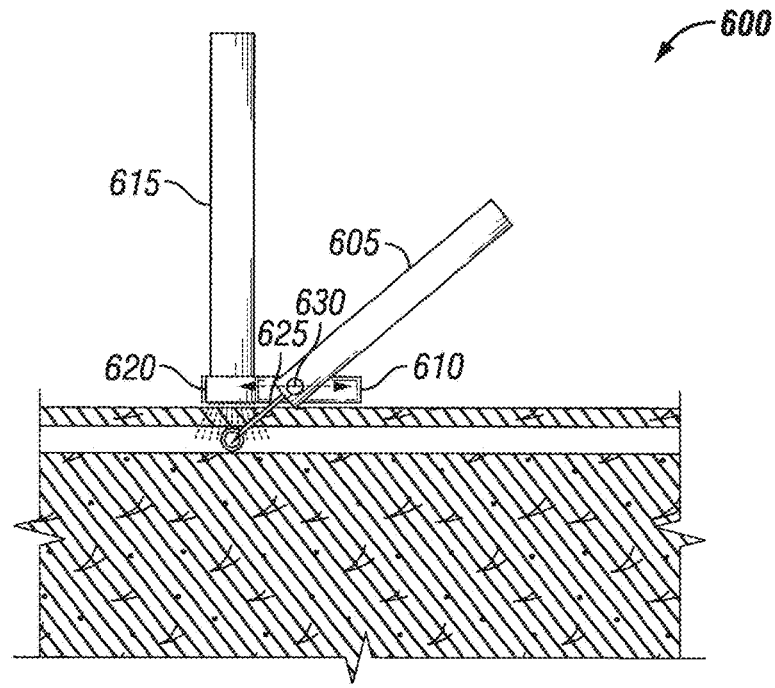
FIGS. 19A-19B are illustrative implementations of a sixth arrangement for an insertion system.
Figure 19B:
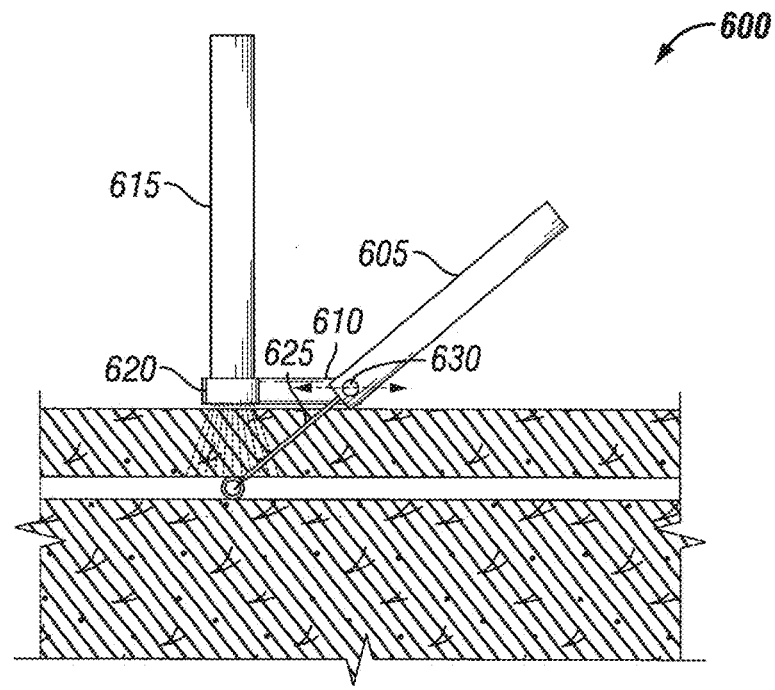

FIGS. 19A and 19B are illustrative implementations of a sixth arrangement for an insertion system 600. In insertion system 600, cartridge 605 has a fixed angle in relation to boom 610. While cartridge 605 is shown independently attached to boom 610, in other implementations, cartridge 605 may be secured to fixed arm in a similar manner as to the articulating arm 45 shown in FIGS. 9A and 9B. Boom 610 is fixed near the bottom of transducer arm 615. Transducer arm 615 provides an attachment for transducer 620. Needle 625 is a variable length needle. Cartridge 605 has a variable pivot point 630 that can be moved along boom 610. The variable pivot point 630 of cartridge 605 and length of needle 625 are adjusted to achieve a desired target depth. A depth scale (not shown) for insertion system 600 takes into account the a variable pivot point 630 and the amount needle 625 has been extended.

From the variety of arrangements discussed above, it should be noted that various arrangements may be also be suitable. For example, any suitable combination of a fixed/variable boom elevation, fixed/variable angle cartridge, fixed/variable needle length, and/or fixed/variable pivot point may be utilized.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A handheld apparatus for accessing a lumen of a vessel, the handheld apparatus comprising:
   an arm providing a cartridge;
   a body providing an image device attachment, wherein said arm is pivotally attached to said body, the image device attachment is positioned adjacent to a pivot point of said arm, and a center of gravity of said handheld apparatus is positioned adjacent to said pivot point where said arm is coupled to said body;
   a slider coupled to the cartridge, wherein said slider secures a needle;
   a slide stop secured to said body; and
   a stop extension extending from said slider, wherein said stop extension contacts said slide stop when said slider is advanced a predetermined length, and said stop extension and slide stop prevent the slider from advancing beyond said predetermined length; wherein the center of gravity of said handheld apparatus is positioned at a point below a midpoint of a height of the handheld apparatus.

2. The handheld apparatus of claim 1, further comprising a depth scale secured to said body, wherein said depth scale provides a scale indicating an insertion depth.

3. The handheld apparatus of claim 2, further comprises:
   a thumb wheel coupled to the arm, wherein rotation of the thumb wheel adjust said arm along said depth scale; and
   an indicator provided by said arm, wherein the indicator specifies said insertion depth on the depth scale.

4. The handheld apparatus of claim 2, wherein said handheld apparatus does not utilize electric power.

5. The handheld apparatus of claim 1, wherein said body provides an arc-like structure, said image capturing instrument is positioned at a center of a width of the handheld apparatus, and a pivot point of said arm is positioned adjacent to an image capturing instrument.

6. The handheld apparatus of claim 5, wherein the center of gravity of said handheld apparatus is positioned at a point adjacent to an axis centered at midpoint of a width of the handheld apparatus.

7. The handheld apparatus of claim 6, wherein the center of gravity of the handheld apparatus is positioned near where the handheld apparatus is held by an operator.

8. The handheld apparatus of claim 1, wherein the image device attachment secures an image capturing instrument, and said image capturing instrument is a preexisting image capturing instrument.

9. The handheld apparatus of claim 1, wherein said cartridge is removable from said arm.

10. The handheld apparatus of claim 1, wherein said cartridge is not removable from said arm.

11. The handheld apparatus of claim 1, wherein pivoting of said arm and advancing said slider is motorized.

12. The handheld apparatus of claim 11, wherein said handheld apparatus is operable with a single hand.

13. The handheld apparatus of claim 1, wherein the said imaging device attachment is an ergonomic handle.

14. The handheld apparatus of claim 13, wherein an image capturing instrument is incorporated into said ergonomic handle.

15. The handheld apparatus of claim 14, wherein one or more controls are positioned on said ergonomic handle, and said handheld apparatus is operable with a single hand.

16. A handheld apparatus for accessing a lumen of a vessel, the handheld apparatus comprising:
    an arm providing a cartridge;
    a body providing an image device attachment, wherein said arm is pivotally attached to said body, the image device attachment is positioned adjacent to a pivot point of said arm;
    a slider coupled to the cartridge, wherein said slider secures a needle; and
    wherein a center of gravity of the handheld apparatus is positioned adjacent to said pivot point, said center of gravity is positioned adjacent to an axis centered on a midpoint of a width of the handheld apparatus, and said center of gravity is positioned below a midpoint of a height of the handheld apparatus.

17. The handheld apparatus of claim 16, further comprising:
    a slide stop secured to said body; and
    a stop extension extending from said slider, wherein said stop extension contacts said slide stop when said slider is advanced a predetermined length, and said stop extension and slide stop prevent the slider from advancing beyond said predetermined length.

18. The handheld apparatus of claim 16, further comprising a depth scale secured to said body, wherein said depth scale provides a scale indicating an insertion depth.

19. The handheld apparatus of claim 16, wherein said handheld apparatus does not utilize electric power.

20. The handheld apparatus of claim 16, wherein the image device attachment secures an image capturing instrument, said image capturing instrument is a preexisting image capturing instrument, and said image capturing instrument is positioned at a center of a width of the handheld apparatus.

21. The handheld apparatus of claim 20, wherein the center of gravity of the handheld apparatus is positioned near where the handheld apparatus is held by an operator.

22. The handheld apparatus of claim 16, wherein pivoting of said arm and advancing said slider is motorized, and said apparatus is operable with a single hand.

* * * * *